(12) United States Patent
Mae et al.

(10) Patent No.: US 7,524,975 B2
(45) Date of Patent: Apr. 28, 2009

US007524975B2

(54) PEROXISOME PROLIFERATOR ACTIVATED RECEPTOR LIGAND AND PROCESS FOR PRODUCING THE SAME

(75) Inventors: Tatsumasa Mae, Kakogawa (JP); Misuzu Tsukagawa, Akashi (JP); Mikio Kitahara, Kobe (JP); Kaku Nakagawa, Kyoto (JP); Shiro Kitamura, Akashi (JP); Yasuyoshi Ueda, Himeji (JP); Minpei Kuroda, Nerima-ku (JP); Yoshihiro Mimaki, Hachioji (JP); Yutaka Sashida, Hachioji (JP)

(73) Assignee: Kaneka Corporation, Osaka (JP)

( * ) Notice: Subject to any disclaimer, the term of this patent is extended or adjusted under 35 U.S.C. 154(b) by 607 days.

(21) Appl. No.: 10/490,641

(22) PCT Filed: Oct. 11, 2002

(86) PCT No.: PCT/JP02/10572

§ 371 (c)(1), (2), (4) Date: Aug. 30, 2004

(87) PCT Pub. No.: WO03/037316

PCT Pub. Date: May 8, 2003

(65) Prior Publication Data

US 2005/0014819 A1     Jan. 20, 2005

(30) Foreign Application Priority Data

| Oct. 11, 2001 | (JP) | ............................. | 2001-313816 |
| Jan. 15, 2002 | (JP) | ............................. | 2002-006304 |
| Feb. 20, 2002 | (JP) | ............................. | 2002-042466 |
| Aug. 2, 2002 | (JP) | ............................. | 2002-226486 |

(51) Int. Cl.
*C07D 311/00* (2006.01)
(52) U.S. Cl. ........................................ 549/405; 549/406
(58) Field of Classification Search ................. 549/289, 549/406, 405
See application file for complete search history.

(56) References Cited

U.S. PATENT DOCUMENTS

| 6,096,364 A | 8/2000 | Bok et al. |
| 2001/0006978 A1 | 7/2001 | Bok et al. |

FOREIGN PATENT DOCUMENTS

| EP | 0 499 015 A1 | 8/1992 |
| EP | 0 920 870 A1 | 6/1999 |
| EP | 1 057 825 A1 | 12/2000 |
| JP | 02-160722 | 6/1990 |
| JP | 03-68517 | 3/1991 |
| JP | 04-297418 | 10/1992 |
| JP | 04 297418 | 10/1992 |
| JP | 06-157277 | 6/1994 |
| JP | 07-165588 | 6/1995 |
| JP | 08-073337 | 3/1996 |
| JP | 2000-86527 | 3/2000 |
| JP | 2000-239176 | 9/2000 |
| JP | 2000-355538 | 12/2000 |
| WO | WO 90/06108 | 6/1990 |
| WO | WO 99/15167 | 4/1999 |
| WO | WO 01/55085 A1 | 8/2001 |

OTHER PUBLICATIONS

Hiraga et al., "Chemical and Original Guide to Licorice Root Products", Meiji Pharm. Univ. Bull., No. 27, pp. 9-57 (1997).

Fukai, et al., "Phenolic Constituents of Licorice" in Progress in the Chemistry of Organic Natural Products, SpringerWien, New York, vol. 73, pp. 1-158 (1998).

Naiwu Fu, et al., "Anti-promoting action and promoter-induced lipid peroxidation inhibiting action of G9315", *Chinese Traditional and Herbal Drugs*, 26(8), pp. 411-413, 422, Aug. 26, 1995.

Ping Zhang, et al., "Recent progression in the pharmacological and clinical research for licorice root and the preparation containing the same", *Chinese Traditional and Herbal Drugs*, 28(9), pp. 568-571, Sep. 28, 1997.

P. J. Harrison, et al., "Naringenin and Hesperetin Reduce Proliferation of the Human Colon Cancer Cell Lines HT 29 and HCT 116," *Federation of American Societies for Experimental Biology (FASEB) Journal*, vol. 15, No. 4, Mar. 7, 2001, p. A630.

Tomohiro Yokota, et al., "The Inhibitory Effect of Giabridin in Hydrophobic Licorice Extracts on Melanogenesis and Inflammation," *Pigment Cell Research*, vol. 9, No. 4., 1996, p. 173.

Snait Tamir, et al. "Estrogen-like activity of glabrene and other constituents isolated from licorice root," *Journal of Steroid Biochemistry and Molecular Biology*, vol. 78, No. 3, Sep. 2001, pp. 291-298.

Cristobal L. Miranda, et al., "Prenylflavonoids from Hops Inhibit the Metabolic Activation of the Carcinogenic Heterocyclic Amine 2-Amino-3-Methylimidazo[4,5-*F*]Quinoline, Mediated by CDNA-Expressed Human CYP1A2", *Drug Metabolism and Disposition*, vol. 28, No. 11, Nov. 2000, pp. 1297-1302.

E.-K. Seo, et al., "Cytotoxic Prenylated Flavanones from *Monotes engleri*," *Phytochemistry*, vol. 45, No. 3, Jun. 1997, pp. 509-515.

(Continued)

*Primary Examiner*—Janet L. Andres
*Assistant Examiner*—Raymond Covington
(74) *Attorney, Agent, or Firm*—Kenyon & Kenyon LLP

(57) ABSTRACT

The present invention easily and efficiently provides a peroxisome proliferator-activated receptor ligand, and a composition for amelioration of insulin resistance or for prevention and/or amelioration of the insulin resistance syndrome containing the same, as an active ingredient. The present invention relates to a peroxisome proliferator-activated receptor ligand which comprises a prenylflavonoid, a chalcone derivative exclusive of prenylflavonoids, a flavonol derivative exclusive of prenylflavonoids, and a salt, a glycoside and/or an esterified substance thereof acceptable as a pharmaceutical preparation or a food or a beverage; a composition containing the above ligand; a plant-derived extract containing the above ligand; and a process for producing the above extract.

1 Claim, No Drawings

OTHER PUBLICATIONS

Tomohiro Yokota, et al., "The Inhibitory Effect of Giabridin from Licorice Extracts on Melanogenesis and Inflammation," *Pigment Cell Research*, vol. 11, 1998, p. 355-361.

Xuejun Pan, et al., "Microwave-assisted extraction of glycyrrhizic acid from licorice root," *Biochemical Engineering Journal*, vol. 5, No. 3, 2000, pp. 173-177.

K. Kajiyama, et al., "Flavonoids and Isoflavonoids of Chemotaxonomic Significance from *Glycyrrhiza pallidiflora* (Leguminosae)," *Biochemical Systematics and Ecology*, vol. 21, No. 8, 1993, pp. 785-793.

Jacob Vaya, et al., "Antioxidant Constituents from Licorice Roots: Isolation, Structure Elucidation and Antioxidative Capacity Toward LDL Oxidation," *Free Radical Biology & Medicine*, vol. 23, No. 2, 1997, pp. 302-313.

Paula A. Belinky, et al., "The antioxidative effects of the isoflavan glabridin on endogenous constituents of LDL during its oxidation," *Atherosclerosis*, vol. 137, No. 1, 1998, pp. 49-61.

Z.-J. Cheng et al., "*Broussochalcone A, a potent antioxidant and effective suppressor of inducible nitric oxide synthase in lipopolysaccharide-activated macrophages*", Biochemical Pharmacology, 61:939-946 (2001).

T. Fukai et al., "*Cytotoxic Activity of Low Molecular Weight Polyphenols against Human Oral Tumor Cell Lines*", Anticancer Research, 20:2525-2536 (2000).

Y. Okada et al., "*Search for Naturally Occuring Substances for Prevention against the Complications of Diabetes Inhibitory Effect on Aldose Reductase and Platelet Aggregation*", International Congress Series, 1157:295-303 (1998).

C.L. Miranda et al., "*Antiproliferative and Cytotoxic Effects of Prenylated Flavonoids from Hops (Humulus lupulus) in Human Cancer Cell Lines*", Food and Chemical Toxicology, 37:271-285 (1999).

M.M. Rafi et al., "Modulation of bcl-2 and Cytotoxicity by Licochalcone-A, a Novel Estrogenic Flavonoid" Anticancer Research, 20(4):2653-2658 (2000).

S. Tamir et al., "*Estrogenic and Antiproliferative Properties of Glabridin from Licorice in Human Breast Cancer Cells*", Cancer Research, 60(20):5704-5709 (2000).

D.S. Weinberg et al., "*Identification and Quantification of Isoflavonoid and Triterpenoid Compliance Markers in a Locorice-Root Extract Power*", J. Agric. Food Chem. 41:42-47 (1993).

I. Haramoto, "*Licorice Extract has an Inhibitory Effect on Melanogenesis and Improves Melasma Other Pigmented Lesions by its Topical Use*", The St. Marianna Medical Journal, 22(6):941-948 (1994) with English abstract on the last page of the document.

M. Rosenblat, et al., "Macrophage enrichment with the isoflaven glabridin inhibits NADPH oxidase-induced cell-mediated oxidation of low density lipoprotein. A possible role for protein kinase C." *Journal of Biological Chemistry*, vol. 274, abstract in p. 13790, May 14, 1999.

K. Aida, et al., "Isoliquiritigenin: A New Aldose Reductase Inhibitor from Glycyrrhizae Radix," *Planta medica*, vol. 56, No. 3, 1990, pp. 254-258.

K.F.R. Santos, et al., "Hypolipidaemic Effects of Naringenin, Rutin, Nicotinic Acid and Their Associations," *Pharmacological Research*, vol. 40, No. 6, 1999, pp. 493-496.

T. Fukai, et al., "An Isoprenylated Flavanone From *Glycyrrhiza glabra* and Rec-assay of Licorice Phenols," *Phytochemistry*, vol. 49, No. 7, 1998, pp. 2005-2013.

Y. Liang, et al., "Suppression of inducible cyclooxygenase and nitric oxide synthase through activation of peroxisome proliferator-activated receptor-γ by flavonoids in mouse macrophages," *Federation of European Biochemical Societies Letters*, vol. 496, 2001, pp. 12-18.

Russian Office Action dated Sep. 9, 2006 with English language translation thereof.

(Abstract only) Suh, et al., "A new ligand for the peroxisome proliferator-activated receptor-gamma (PPAR-gamma), GW7845, inhibits rat mammary carcinogenesis", Cancer Res., vol. 59, No. 22, pp. 5671-5673, (Nov. 15, 1999).

(Abstract only) Maggi, et al., "Anti-inflammatory actions of 15-deoxy-delta 12, 14-prostaglandin J2 and troglitazone: evidence for heat shock-dependent and—independent inhibiton of cytokine-induced inducible nitric oxide synthase expression", Diabetes, vol. 49, No. 3, pp. 346-355, (Mar. 2000).

(Abstract only) Shibata, S., "Anti-tumorigenic chalcones", Stem Cells, vol. 12, No. 1, pp. 44-52, (Jan. 1994).

(Abstract only) Iwashita, et al., "Flavonoids inhibit cell growth and induce apoptosis in B16 melanoma 4A5 cells", Biosci Biotechnol Biochem, vol. 64, No. 9, pp. 1813-1820, (Sep. 2000).

M.Z. Sitohy et al., "Metabolic effects of licorice roots (*Glycyrrhiza glabra*) on lipid distribution pattern, liver and renal functions of albino rats." Die Nahrung 35 (1991) 8, 709-806.

Yumiko Fujisawa et al., "Glycyrrhizin inhibits the lytic pathway of complement—Possible mechanism of its anti-inflammatory effect on liver cells in viral hepatitis." Microbiol. Immunol. 44(9), 709-804, 2000.

E.A. Davis et al., "Medicinal uses of licorice through the millenia: the good and plenty of it." Molecular and Cellular Endocrinology, 78 (1991) 1-6.

J. I. Cohen, "Licking latency with licorice", The Journal of Clinical Investigation, vol. 115, No. 3, 2005.

Toshi Fukai et al., "Isoprenylated flavonoids from underground parts of *Glycyrrhiza glabra*." Phytochemistry, 43 (5): 1119-1124, Dec. 1996.

PEROXISOME PROLIFERATOR ACTIVATED RECEPTOR LIGAND AND PROCESS FOR PRODUCING THE SAME

This application is a 371 national phase application of PCT/JP02/10572 filed on 11 Oct. 2002, claiming priority to JP 2001-313816, filed on 11 Oct. 2001, JP-2002-6304 filed 15 Jan. 2002, JP 2002-42466 filed 20 Feb. 2002, and JP 2002-226486 filed 2 Aug. 2002, the contents of which are incorporated herein by reference in their entirety.

TECHNICAL FIELD

The present invention relates to a peroxisome proliferator-activated receptor ligand, a process for producing the same, and a composition for amelioration of insulin resistance or for prevention and/or amelioration of the insulin resistance syndrome (type 2 diabetes, hyperinsulinemia, dyslipidemia, obesity, hypertension and arteriosclerotic disease) containing the peroxisome proliferator-activated receptor ligand as an active ingredient.

BACKGROUND ART

Peroxisome proliferator-activated receptor (PPAR) is a ligand-dependent transcription regulator belonging to an intranuclear receptor family. This family is identified as a family of transcription regulators involved in regulating expression of a lipid metabolism-maintaining gene group. In mammalian animals, the presence of 3 subtypes, i.e. PPARα, PPARδ (PPARβ, NUC-1, FAAR) and PPARγ, is known, and PPARα is expressed mainly in the liver and PPARδ is universally expressed. For PPARγ, there are 2 isoforms, i.e. PPARγ1 and PPARγ2, and PPARγ1 is expressed not only in an adipose tissue but also in an immune organ, adrenal gland and small intestine. PPARγ2 is expressed specifically in an adipose tissue, and is a master regulator which regulates differentiation and maturation of an adipocyte (Teruo Kawada, "Igaku No Ayumi", 184, 519-523, 1998).

As PPARγ ligands, synthetic compounds including thiazolidine derivatives such as troglitazone, pioglitazone and rosiglitazone are known. As PPARγ ligands, naturally occurring compounds including arachidonic acid metabolites such as 15-deoxy-$\Delta^{12,14}$-prostaglandin $J_2$ and $\Delta^{12}$-prostaglandin $J_2$, unsaturated fatty acids such as ω-3 multivalent unsaturated fatty acid, x-linolenic acid, eicosapentaenoic acid (EPA) and docosahexaenoic acid (DHA), and eicosanoids such as 9-hydroxyoctadecadienoic acid and 13-hydroxyoctadecadienoic acid are known (J. Auwerx, Diabetologia, 42, 1033-1049, 1999). Japanese Kokai Publication 2000-355538 discloses a $C_{10-26}$ conjugated unsaturated fatty acid having a conjugated triene structure or a conjugated tetraene structure. For flavonoids, chrysin and apigenin as flavone derivatives and kaempferol as a flavonol derivative are reported to be PPARγ ligands (Y. C. Liang, et al., FEBS Letters, 496, 12-18, 2001). A flavonoid is a component contained widely in plants, and is known to have antioxidant properties. However, it is not known that a prenylflavonoid contained only in a specific plant is a PPARγ ligand.

The agonistic activity of a thiazolidine derivative as PPARγ ligand is correlated with its hypoglycemic action, thus the derivative has attracted attention for its relationship with an ameliorating action on insulin resistance and been developed as an insulin resistance ameliorator for type 2 diabetes mellitus (non-insulin dependent diabetes mellitus: NIDDM). That is, a thiazolidine derivative, which is a PPARγ ligand, activates PPARγ thereby increasing a normally functioning small adipocyte differentiated from a preadipocyte. Thereafter, a hypertrophic adipocyte, in which over-production and over-secretion of TNFα and a free fatty acid inducing insulin resistance, is reduced with apotosis. As a result, insulin resistance is ameliorated (A. Okuno, et al., Journal of Clinical Investigation, 101, 1354-1361, 1998). A PPARγ ligand ameliorates insulin resistance and is thus also effective in preventing and/or ameliorating the insulin resistance syndrome including not only type 2 diabetes mellitus but also hyperinsulinemia, dyslipidemia, obesity (in particular visceral fat obesity), hypertension and arteriosclerosis (R. A. DeFronzo & E. Ferrannini, Diabetes Care, 14, 173-194, 1991). Pathologic conditions in the same category as the insulin resistance syndrome include Syndrome X (G. M. Reaven, Diabetes, 37, 1595-1607, 1988), the deadly quartet (N. M. Kaplan, Archives of Internal Medicine, 149, 1514-1520, 1989) and the visceral fat syndrome (Y. Matsuzawa, Diabetes/Metabolism Reviews, 13, 3-13, 1997).

A PPARγ ligand is also effective in preventing and/or ameliorating inflammations and cancers because of its inhibition of inflammatory cytokine production (C. Jiang, et al., Nature, 391, 82-86, 1998) and its induction of apotosis thereby inhibiting growth of cancer cells (Y. Tsubouchi, et al., Biochemical and Biophysical Research Communications, 270, 400-405, 2000).

SUMMARY OF THE INVENTION

In view of the foregoing, a PPARγ ligand has an effect on amelioration of insulin resistance, and on prevention and/or amelioration of the insulin resistance syndrome such as type 2 diabetes mellitus, hyperinsulinemia, dyslipidemia, obesity (in particular visceral fat obesity), hypertension and arteriosclerosis. The object of the present invention is to provide a PPAR ligand found in naturally occurring materials, a process for easily and efficiently producing the same, and a composition for amelioration of insulin resistance or for prevention and/or amelioration of the insulin resistance syndrome containing the ligand as an active ingredient.

The present inventors searched for a substance having a PPARγ ligand activity from eatable naturally occurring materials, and as a result, they found that an extract of plant such as licorice has a PPARγ ligand activity. The present inventors intensively studied its active ingredient, and as a result they found that a specific component in the extract has a PPARγ ligand activity. Furthermore, the present inventors found that an organic solvent, preferably a fatty acid ester or a water-soluble organic solvent, particularly a water-soluble organic solvent, can be used to efficiently extract such a component from licorice, to complete the present invention.

That is, the first aspect of the invention is concerned with a peroxisome proliferator-activated receptor ligand which comprises a prenylflavonoid, a chalcone derivative exclusive of prenylflavonoids, a flavonol derivative exclusive of prenylflavonoids, and a salt, a glycoside and/or an esterified substance thereof acceptable as a pharmaceutical preparation or a food or a beverage.

The second aspect of the invention is concerned with a plant-derived extract which comprises a peroxisome proliferator-activated receptor ligand comprising a prenylflavonoid, a chalcone derivative exclusive of prenylflavonoids, a flavonol derivative exclusive of prenylflavonoids, and a salt, a glycoside and/or an esterified substance thereof acceptable as a pharmaceutical preparation or a food or a beverage.

The third aspect of the invention is concerned with a composition for amelioration of insulin resistance or for prevention and/or amelioration of the insulin resistance syndrome which comprises, as an active ingredient, a prenylflavonoid having an ability to bind to a ligand-binding region of a peroxisome proliferator-activated receptor, a chalcone derivative exclusive of prenylflavonoids, a flavonol derivative exclusive of prenylflavonoids, and a salt, a glycoside and/or an esterified substance thereof acceptable as a pharmaceutical preparation or a food or a beverage.

The fourth aspect of the invention is concerned with a composition for prevention and/or amelioration of inflammations and cancers which comprises, as an active ingredient, a prenylflavonoid having an ability to bind to a ligand-binding region of a peroxisome proliferator-activated receptor, a chalcone derivative exclusive of prenylflavonoids, a flavonol derivative exclusive of prenylflavonoids, and a salt, a glycoside and/or an esterified substance thereof acceptable as a pharmaceutical preparation or a food or a beverage.

The fifth aspect of the invention is concerned with a process for producing the extract described above which comprises extracting the extract from licorice having the ratio of the skin area to the whole surface area of 30% or more.

The sixth aspect of the invention is concerned with a process for producing the extract described above wherein the extraction from licorice is carried out with a fatty acid ester or a water-soluble organic solvent.

The seventh aspect of the invention is concerned with a process for producing the extract described above which comprises extracting from licorice with an organic solvent having a water content of 30% by volume or less.

DETAILED DESCRIPTION OF THE INVENTION

Hereinafter, embodiments of the present invention are described in detail.

A PPAR ligand (preferably a PPARγ ligand) is a compound having PPAR ligand activity (preferably PPARγ ligand activity), that is, a compound having an ability to bind to a ligand-binding region of PPAR (preferably PPARγ). PPARγ ligand activity can be measured by, for example, a reporter assay wherein a binding of the compound to a fusion protein of a PPARγ ligand-binding region and GAL4 is evaluated in terms of expression of luciferase (B. M. Forman, et al., Cell, 83, 803-812, 1995), competition binding assay using a protein having a PPARγ ligand-binding region (S. A. Kliewer, et al., Cell, 83, 813-819, 1995), etc. Generally, activity of a sample is compared with that of a solvent control in these assays, and a sample exhibiting higher activity than that of the solvent control and also recognized that the activity is dose-dependent is defined as the one having "PPARγ ligand activity."

The PPAR ligand, preferably the PPARγ ligand, of the present invention is at least one compound selected from the group consisting of a prenylflavonoid, a chalcone derivative exclusive of prenylflavonoids, a flavonol derivative exclusive of prenylflavonoids, and a salt, a glycoside and an esterified substance thereof acceptable as a pharmaceutical preparation or a food or a beverage.

The salt acceptable as a pharmaceutical preparation or a food or a beverage includes, but is not limited to, sodium salts, potassium salts, magnesium salts, calcium salts, etc., for example.

The glycoside acceptable as a pharmaceutical preparation or a food or a beverage includes, but is not limited to, glycosides of monosaccharides such as glucose and galactose, glycosides of disaccharides or oligosaccharides, etc., for example.

The esterified substance acceptable as a pharmaceutical preparation or a food or a beverage includes, but is not limited to, acetates, propionates, phosphates, sulfates, etc., for example.

The composition of the present invention comprising, as an active ingredient, at least one species selected from these compounds ameliorates insulin resistance, and is thus useful as an agent for prevention and/or amelioration of the insulin resistance syndrome including diabetes mellitus.

The prenylflavonoid, which is the PPAR ligand of the present invention, is not particularly limited, but is preferably at least one compound selected from the group consisting of a 3-arylcoumarin derivative, an isoflav-3-ene derivative, an isoflavan derivative, an isoflavanone derivative, an isoflavone derivative, a flavonol derivative, a flavanone derivative, a chalcone derivative and a dibenzoylmethane derivative.

The prenylflavonoid as referred herein is defined to be a compound having at least one of the following. (A) and (B) as a side chain of flavonoid: (A) a prenyl group, or (B) a structure having a 6-membered ring in which a prenyl group is bound to its adjacent hydroxyl group to form [—CH=CHC(CH$_3$)$_2$O—]. The term "flavonoid" is a generic term of a group of substances having 2 phenyl groups bound each other via 3 carbon atoms, and examples thereof include flavone, flavonol, flavanone, flavanonol, isoflavone, isoflavonol, isoflavanone, isoflavan, isoflav-3-ene, 3-arylcoumarin, chalcone, dihydrochalcone, dibenzoylmethane, coumestan, pterocarpan, catechin, anthocyanidin, etc.

The 3-arylcoumarin derivative, which is a prenylflavonoid used in the present invention, is not particularly limited, but preferable examples thereof include compounds represented by the following general formula (1). And for example, compounds shown in Table 1 such as glycycoumarin, glycyrin, gancaonin W, glyasperin L, kanzonol W, etc. may be mentioned. Derivatives thereof such as salts, glycosides and esterified substances may also be mentioned. Among these, glycycoumarin and glycyrin are more preferable.

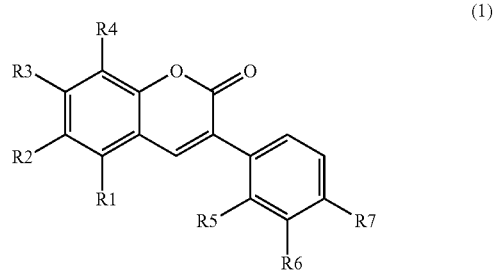

(1)

In the formula, at least one of R1 to R7 represents a prenyl group or a structure wherein adjacent 2 R groups form a 6-membered ring comprising —CH=CHC(CH$_3$)$_2$O—, and other R groups represent H, OH or OCH$_3$.

TABLE 1

| R1 | R2 | R3 | R4 | R5 | R6 | R7 | 3-Arylcoumarin(s) |
|---|---|---|---|---|---|---|---|
| OCH$_3$ | prenyl | OH | H | OH | H | OH | glycycoumarin |
| OCH$_3$ | prenyl | OCH$_3$ | H | OH | H | OH | glycyrin |
| OCH$_3$ | H | OH | H | OH | prenyl | OH | gancaonin W |
| OCH$_3$ | H | OH | H | OH | —CH=CHC(CH$_3$)$_2$O— | | glyasperin L |
| H | H | —OC(CH$_3$)$_2$CH=CH— | | OH | H | OH | kanzonol W |
| H | H | —OC(CH$_3$)$_2$CH=CH— | | OH | H | OCH$_3$ | RL-P |
| H | H | OH | H | —OC(CH$_3$)$_2$CH=CH— | | OH | RL-U |

The isoflav-3-ene derivative that is a prenylflavonoid used in the present invention is not particularly limited, but preferable examples thereof include compounds represented by the following general formula (2). For example, compounds shown in Table 2 such as dehydroglyasperin C, dehydroglyasperin D, glabrene and RL-S. Derivatives thereof such as salts, glycosides and esterified substances may also be mentioned. Among these, dehydroglyasperin C, dehydroglyasperin D and glabrene are more preferable. Dehydroglyasperin D is a novel compound found for the first time in the present invention.

salts, glycosides and esterified substances may also be mentioned. Among these, glyasperin D, glabridin, hispaglabridin B, 4'-O-methylglabridin and 3'-hydroxy-4'-O-methylglabridin are more preferable.

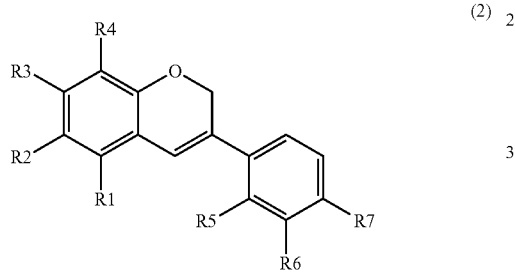

(2)

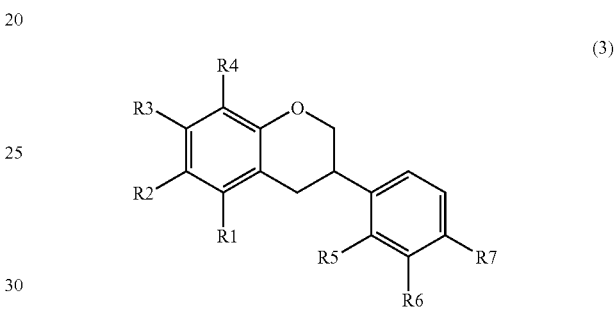

(3)

In the formula, at least one of R1 to R7 represents a prenyl group or a structure wherein adjacent 2 R groups form a 6-membered ring comprising —CH=CHC(CH$_3$)$_2$O—, and other R groups represent H, OH or OCH$_3$.

In the formula, at least one of R1 to R7 represents a prenyl group or a structure wherein adjacent 2 R groups form a 6-membered ring comprising —CH=CHC(CH$_3$)$_2$O—, and other R groups represent H, OH or OCH$_3$.

TABLE 2

| R1 | R2 | R3 | R4 | R5 | R6 | R7 | Isoflav-3-ene(s) |
|---|---|---|---|---|---|---|---|
| OCH$_3$ | prenyl | OH | H | OH | H | OH | dehydroglyasperin C |
| OCH$_3$ | prenyl | OCH$_3$ | H | OH | H | OH | dehydroglyasperin D |
| H | H | OH | H | —OC(CH$_3$)$_2$CH=CH— | | OH | glabrene |
| H | H | —OC(CH$_3$)$_2$CH=CH— | | OH | H | OH | RL-S |

The isoflavan derivative that is a prenylflavonoid used in the present invention is not particularly limited, but preferable examples thereof include compounds represented by the following general formula (3). For example, compounds shown in Table 3 such as glyasperin C, glyasperin D, glyasperin I, licoricidin and licorisoflavan A. Derivatives thereof such as

TABLE 3

| R1 | R2 | R3 | R4 | R5 | R6 | R7 | Isoflavan(s) |
|---|---|---|---|---|---|---|---|
| OCH$_3$ | prenyl | OH | H | OH | H | OH | glyasperin C |
| OCH$_3$ | prenyl | OCH$_3$ | H | OH | H | OH | glyasperin D |
| OCH$_3$ | prenyl | OH | H | OCH$_3$ | H | OH | glyasperin I |
| OCH$_3$ | prenyl | OH | H | OH | prenyl | OH | licoricidin |
| OCH$_3$ | prenyl | OCH$_3$ | H | OH | prenyl | OH | licorisoflavan A |
| OCH$_3$ | prenyl | OCH$_3$ | H | —OC(CH$_3$)$_2$CH=CH— | | OH | kanzonol I |

TABLE 3-continued

| R1 | R2 | R3 | R4 | R5 | R6 | R7 | Isoflavan(s) |
|---|---|---|---|---|---|---|---|
| H | prenyl | OH | H | —OC(CH$_3$)$_2$CH=CH— | | OH | glyinflanin I |
| H | —CH=CHC(CH$_3$)$_2$O— | | H | OH | H | OCH$_3$ | gancaonin X |
| OCH$_3$ | —CH=CHC(CH$_3$)$_2$O— | | H | OH | prenyl | OCH$_3$ | kanzonol H |
| OCH$_3$ | —CH=CHC(CH$_3$)$_2$O— | | H | —OC(CH$_3$)$_2$CH=CH— | | OCH$_3$ | kanzonol J |
| H | —CH=CHC(CH$_3$)$_2$O— | | H | —OC(CH$_3$)$_2$CH=CH— | | H | glyinflanin J |
| H | H | OH | H | OH | prenyl | OCH$_3$ | gancaonin Z |
| OCH$_3$ | H | OH | H | OH | prenyl | OCH$_3$ | kanzonol R |
| H | H | OH | prenyl | OH | prenyl | OH | kanzonol X |
| H | H | —OC(CH$_3$)$_2$CH=CH— | | OH | H | OH | glabridin |
| H | H | —OC(CH$_3$)$_2$CH=CH— | | OH | H | OCH$_3$ | 4'-O-methylglabridin |
| H | H | —OC(CH$_3$)$_2$CH=CH— | | OH | OH | OCH$_3$ | 3'-hydroxy-4'-O-methyl-glabridin |
| H | H | —OC(CH$_3$)$_2$CH=CH— | | OH | OCH$_3$ | OH | 3'-O-methylglabridin |
| H | H | —OC(CH$_3$)$_2$CH=CH— | | OCH$_3$ | OH | OCH$_3$ | glyasperin H |
| H | H | —OC(CH$_3$)$_2$CH=CH— | | OH | prenyl | OH | hispaglabridin A |
| H | H | —OC(CH$_3$)$_2$CH=CH— | | OH | —CH=CHC(CH$_3$)$_2$O— | | hispaglabridin B |
| H | H | —OC(CH$_3$)$_2$CH=CH— | | OCH$_3$ | —CH=CHC(CH$_3$)$_2$O— | | methylhispaglabridin B |
| H | H | —OC(CH$_3$)$_2$CH=CH— | | —OC(CH$_3$)$_2$CH=CH— | | H | glyinflanin K |
| H | H | OH | H | —OC(CH$_3$)$_2$CH=CH— | | OCH$_3$ | gancaonin Y |
| H | H | OH | H | OH | —CH=CHC(CH$_3$)$_2$O— | | phaseollinisoflavan |
| H | H | OH | prenyl | OH | —CH=CHC(CH$_3$)$_2$O— | | 8-prenyl-phaseollinisoflavan |

The isoflavanon derivative that is a prenylflavonoid used in the present invention is not particularly limited, but preferable examples thereof include compounds represented by the following general formula (4). For example, compounds shown in Table 4 such as glyasperin B, glyasperin K, kanzonol G, 3'-prenyl-kievitone and glyasperin F. Derivatives thereof such as salts, glycosides and esterified substances may also be mentioned. Among these, glyasperin B and glycyrrhisoflavanone are more preferable.

The isoflavon derivative that is a prenylflavonoid used in the present invention is not particularly limited, but preferable examples thereof include compounds represented by the following general formula (5). For example, compounds shown in Table 5 such as wighteone, gancaonin A, gancaonin B, gancaonin G and gancaonin N. Derivatives thereof such as salts, glycosides and esterified substances may also be mentioned. Among these, glyurallin B, lupiwighteone, semilicoisoflavone B and glycyrrhisoflavone are more preferable.

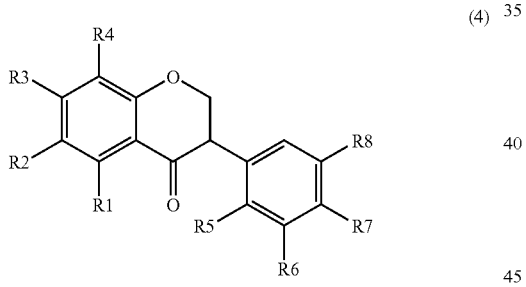

(4)

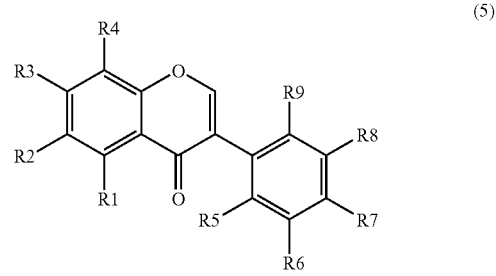

(5)

In the formula, at least one of R1 to R8 represents a prenyl group or a structure wherein adjacent 2 R groups form a 6-membered ring comprising —CH=CHC(CH$_3$)$_2$O—, and other R groups represent H, OH or OCH$_3$.

In the formula, at least one of R1 to R9 represents a prenyl group or a structure wherein adjacent 2 R groups form a 6-membered ring comprising —CH=CHC(CH$_3$)$_2$O—, and other R groups represent H, OH or OCH$_3$.

TABLE 4

| R1 | R2 | R3 | R4 | R5 | R6 | R7 | R8 | Isoflavanone(s) |
|---|---|---|---|---|---|---|---|---|
| OH | prenyl | OCH$_3$ | H | OH | H | OH | H | glyasperin B |
| OH | prenyl | OCH$_3$ | H | OH | H | OCH$_3$ | H | glyasperin K |
| OH | prenyl | OCH$_3$ | H | OH | prenyl | OH | H | kanzonol G |
| OH | H | OH | prenyl | OH | prenyl | OH | H | 3'-prenyl-kievitone(3',8-diprenyldalbergioidin) |
| OH | H | OH | H | —OC(CH$_3$)$_2$CH=CH— | | OH | H | glyasperin F |
| OH | H | OH | prenyl | —OC(CH$_3$)$_2$CH=CH— | | OH | H | glyasperin J |
| OCH$_3$ | H | OH | H | H | OH | —CH=CHC(CH$_3$)$_2$O— | | glycyrrhisoflavanone |
| OCH$_3$ | H | OH | H | OH | —CH=CHC(CH$_3$)$_2$O— | | H | glyasperin M |
| OH | H | OH | H | OH | —CH=CHC(CH$_3$)$_2$O— | | H | licoisoflavanone |
| H | H | —OC(CH$_3$)$_2$CH=CH— | | OH | H | OH | H | RL-Q |
| H | H | —OC(CH$_3$)$_2$CH=CH— | | OH | H | OCH$_3$ | H | RL-R |
| OH | prenyl | OH | H | OH | prenyl | OH | H | No Name |

TABLE 5

| R1 | R2 | R3 | R4 | R5 | R6 | R7 | R8 | R9 | Isoflavone(s) |
|---|---|---|---|---|---|---|---|---|---|
| OH | prenyl | OH | H | H | H | OH | H | H | wighteone |
| OH | prenyl | OH | H | H | H | OCH$_3$ | H | H | gancaonin A |
| OH | prenyl | OH | H | H | OH | OCH$_3$ | H | H | gancaonin B |
| OH | prenyl | OCH$_3$ | H | H | H | OH | H | H | gancaonin G |
| OH | prenyl | OH | H | OH | H | OCH$_3$ | H | H | gancaonin N |
| OH | prenyl | OCH$_3$ | H | OH | H | OH | H | H | 7-O-methylluteone |
| OH | prenyl | OCH$_3$ | H | OH | prenyl | OH | H | H | kanzonol K |
| OH | prenyl | OH | prenyl | —OC(CH$_3$)$_2$CH=CH— | | OH | H | H | kanzonol L |
| OH | prenyl | OH | H | H | OH | OH | prenyl | H | isoangustone A |
| OH | prenyl | OH | H | H | OH | —OC(CH$_3$)$_2$CH=CH— | | H | gancaonin H |
| OH | H | OH | prenyl | H | H | OH | H | H | lupiwighteone |
| OH | H | OH | prenyl | H | OH | OH | H | H | gancaonin L |
| OH | H | OH | prenyl | H | H | OCH$_3$ | H | H | gancaonin M |
| OH | H | OH | prenyl | H | OH | OH | prenyl | H | glyurallin B |
| OH | H | OH | prenyl | —OC(CH$_3$)$_2$CH=CH— | | OH | H | H | glyasperin N |
| H | H | OH | H | OH | prenyl | OH | H | H | eurycarpin A |
| OH | H | OH | H | OH | prenyl | OH | H | H | licoisoflavone A |
| OH | H | OH | H | OH | —CH=CHC(CH$_3$)$_2$O— | | H | H | licoisoflavone B |
| H | H | OH | H | OH | —CH=CHC(CH$_3$)$_2$O— | | H | H | glabrone |
| OH | H | OH | H | H | OH | OH | prenyl | H | glycyrrhisoflavone |
| OCH$_3$ | H | OH | H | H | OH | OH | prenyl | H | glisoflavone |
| OH | H | OH | H | H | OH | —OC(CH$_3$)$_2$CH=CH— | | H | semilicoisoflavone B |
| H | H | OH | H | OH | H | OH | prenyl | OCH$_3$ | glicoricone |
| H | H | OH | H | OH | H | OCH$_3$ | prenyl | OCH$_3$ | licoricone |

The flavonol derivative that is a prenylflavonoid used in the present invention is not particularly limited, but preferable examples thereof include compounds represented by the following general formula (6). For example, compounds shown in Table 6 such as licoflavonol, gancaonin P, topazolin, glyasperin A and isolicoflavonol. Derivatives thereof such as salts, glycosides and esterified substances may also be mentioned. Among these, isolicoflavonol, licoflavonol and topazolin are more preferable.

The flavanone derivative that is a prenylflavonoid used in the present invention is not particularly limited, but preferable examples thereof include compounds represented by the following general formula (7). For example, compounds shown in Table 7 such as 6-prenylpinocembrin, 6-prenylnaringenin, 6-prenyleriodictyol, sinoflavanone B and paratocarpin L. Derivatives thereof such as salts, glycosides and esterified substances may also be mentioned. Among these, glabrol is more preferable.

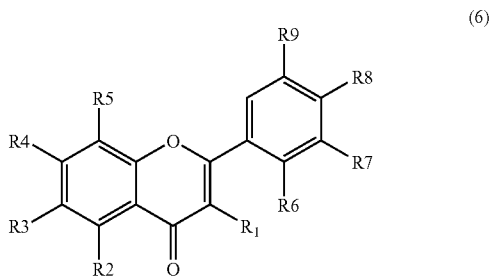

(6)

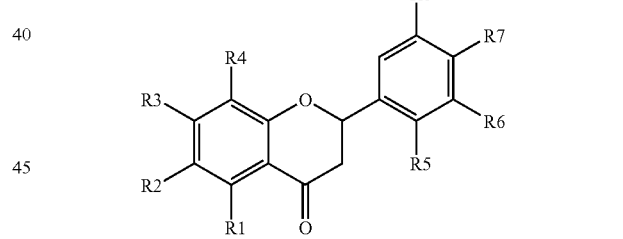

(7)

In the formula, R1 is OH or OCH$_3$, at least one of R2 to R9 represents a prenyl group or a structure wherein adjacent 2 R groups form a 6-membered ring comprising —CH=CHC(CH$_3$)$_2$O—, and other R groups represent H, OH or OCH$_3$.

In the formula, at least one of R1 to R8 represents a prenyl group or a structure wherein adjacent 2 R groups form a

TABLE 6

| R1 | R2 | R3 | R4 | R5 | R6 | R7 | R8 | R9 | Flavonol(s) |
|---|---|---|---|---|---|---|---|---|---|
| OH | OH | prenyl | OH | H | H | H | OH | H | licoflavonol |
| OH | OH | prenyl | OH | H | H | OH | OH | H | gancaonin P |
| OCH$_3$ | OH | prenyl | OH | H | H | H | OH | H | topazolin |
| OH | OH | prenyl | OH | H | H | prenyl | OH | H | glyasperin A |
| OH | OH | H | OH | H | H | prenyl | OH | H | isolicoflavonol |
| OH | OH | H | OH | prenyl | H | H | H | H | glepidotin A |
| OH | H | OH | OH | H | prenyl | OH | OH | H | neouralenol |
| OH | OH | H | OH | H | H | OH | OH | prenyl | uralenol |
| OCH$_3$ | OH | H | OH | H | H | OH | OH | prenyl | uralenol-3-O-methyl-ether |
| OCH$_3$ | OH | OH | H | H | H | OH | OH | prenyl | uralane |

6-membered ring comprising —CH═CHC(CH₃)₂O—, and other R groups represent H, OH or OCH₃.

TABLE 7

| R1 | R2 | R3 | R4 | R5 | R6 | R7 | R8 | Flavanone(s) |
|---|---|---|---|---|---|---|---|---|
| OH | prenyl | OH | H | H | H | H | H | 6-prenylpinocembrin |
| OH | prenyl | OH | H | H | H | OH | H | 6-prenylnaringenin |
| OH | prenyl | OH | H | H | OH | OH | H | 6-prenyleriodictyol |
| OH | prenyl | OH | prenyl | H | H | H | H | sinoflavanone B |
| OH | prenyl | OH | H | H | prenyl | OH | H | paratocarpin L |
| H | H | OH | prenyl | H | H | H | H | ovaliflavanone B |
| H | H | OH | prenyl | H | H | OH | H | isobavachin |
| OH | H | OH | prenyl | H | H | H | H | glabranin |
| OH | H | OH | prenyl | H | H | OH | H | sophoraflavanone B |
| OH | H | OH | prenyl | H | OH | OH | H | 8-prenyleriodictyol |
| OH | H | OH | prenyl | H | OCH₃ | OH | H | exiguaflavanone K |
| H | H | OH | prenyl | H | prenyl | OH | H | glabrol |
| OH | H | OH | prenyl | H | prenyl | OH | H | euchrestaflavanone A |
| OH | H | OH | prenyl | H | OH | OH | prenyl | gancaonin E |
| OH | H | —OC(CH₃)₂CH═CH— | | H | H | OH | H | citflavanone |
| H | H | —OC(CH₃)₂CH═CH— | | H | prenyl | OH | H | shinflavanone |
| H | H | —OC(CH₃)₂CH═CH— | | H | —CH═CHC(CH₃)₂O— | | H | xambioona |
| OH | H | OH | H | H | prenyl | OH | H | licoflavanone |
| OH | H | OH | H | H | OH | OH | prenyl | sigmoidin B (uralenin) |
| OH | H | OH | H | H | H | —OC(CH₃)₂CH═CH— | | sigmoidin C |
| H | prenyl | OH | prenyl | H | H | OH | H | No Name |

The chalcone derivative that is a prenylflavonoid used in the present invention is not particularly limited, but preferable examples thereof include compounds represented by the following general formula (8). For example, compounds shown in Table 8 such as licochalcone C, licochalcone D, glyinflanin G, kanzonol B and kanzonol C. Derivatives thereof such as salts, glycosides and esterified substances may also be mentioned. Among these, licochalcone C is more preferable.

The dibenzoylmethane derivative that is a prenylflavonoid used in the present invention is not particularly limited, but preferable examples thereof include compounds represented by the following general formula (9). For example, compounds shown in Table 9 such as glycyrdione A, glycyrdione B, glycyrdione C, glyinflanin B and glyinflanin D. Derivatives thereof such as salts, glycosides and esterified substances may also be mentioned. Among these, glycyrdione A and glycyrdione C are more preferable.

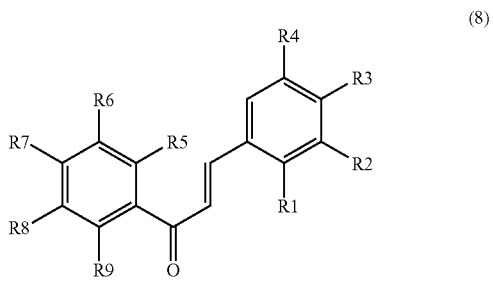

(8)

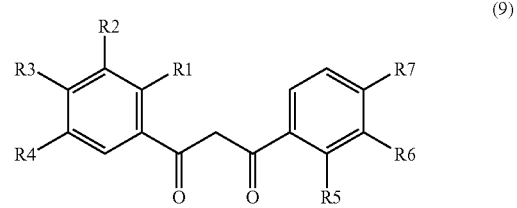

(9)

In the formula, at least one of R1 to R9 represents a prenyl group or a structure wherein adjacent 2 R groups form a 6-membered ring comprising —CH═CHC(CH₃)₂O—, and other R groups represent H, OH or OCH₃.

In the formula, at least one of R1 to R7 represents a prenyl group or a structure wherein adjacent 2 R groups form a 6-membered ring comprising —CH═CHC(CH₃)₂O—, and other R groups represent H, OH or OCH₃.

TABLE 8

| R1 | R2 | R3 | R4 | R5 | R6 | R7 | R8 | R9 | Chalcone(s) |
|---|---|---|---|---|---|---|---|---|---|
| OCH₃ | prenyl | OH | H | H | H | OH | H | H | licochalcone C |
| OCH₃ | OH | OH | H | H | prenyl | OH | H | H | licochalcone D |
| H | —CH═CHC(CH₃)₂O— | | OH | OH | —CH═CHC(CH₃)₂O— | | H | H | glyinflanin G |
| H | —CH═CHC(CH₃)₂O— | | H | OH | H | OH | H | H | kanzonol B |
| H | prenyl | OH | H | H | H | OH | prenyl | OH | kanzonol C |
| H | H | OH | H | OH | H | OCH₃ | prenyl | H | isobavachalcone |
| H | prenyl | OH | H | OH | prenyl | OH | H | H | No Name |
| H | OH | —OC(CH₃)₂CH═CH— | | OH | prenyl | OH | H | H | No Name |
| H | —CH═CHC(CH₃)₂O— | | OH | H | H | OH | prenyl | OH | No Name |

TABLE 9

| R1 | R2 | R3 | R4 | R5 | R6 | R7 | Dibenzoylmethane(s) |
|---|---|---|---|---|---|---|---|
| OH | H | OH | prenyl | H | prenyl | OH | glycyrdione A (glyinflanin A) |
| OH | H | OH | prenyl | H | —CH=CHC(CH₃)₂O— | | glycyrdione B |
| OH | H | —OC(CH₃)₂CH=CH— | | H | prenyl | OH | glycyrdione C (glyinflanin C) |
| OH | H | —OC(CH₃)₂CH=CH— | | H | H | OH | glyinflanin B |
| OH | H | —OC(CH₃)₂CH=CH— | | H | —CH=CHC(CH₃)₂O— | | glyinflanin D |
| OH | H | OH | H | H | prenyl | OH | kanzonol A |
| OH | H | OH | prenyl | H | H | OH | 5'-prenyl-licodione |

The chalcone derivative exclusive of prenylflavonoids used in the present invention is not particularly limited, but preferable examples thereof include echinatin, isoliquiritigenin, licochalcone A and licochalcone B. Derivatives thereof such as salts, glycosides and esterified substances may also be mentioned.

The flavonol derivative exclusive of prenylflavonoids used in the present invention is not particularly limited, but preferable examples thereof include kaempferol 3-O-methylester. Derivatives thereof such as salts, glycosides and esterified substances may also be mentioned.

For names of these compounds, a report of T. Hiraga & K. Kajiyama (Meiji Pharmaceutical University Bulletin, 27, 9-57, 1997) and a report of T. Nomura & T. Fukai (Fortschritte der Chemie organischer Naturstoffe, 73, 1-158, 1998) were referred to.

The PPAR ligand of the present invention may be any compound derived from natural sources such as plants, chemically synthesized or biosynthesized in cultured cells, etc., if the compound is the above compound, but is preferably a compound derived from natural sources which human can eat. The method for obtaining these compounds is not particularly limited, and the compounds can be obtained from licorice of the Leguminosae family which human can eat, or from other plants. The other plants mentioned above are not particularly limited provided that the plants contain the PPAR ligand, preferably the PPARγ ligand, and in addition to the plants of the Leguminosae family, and plants of the Moraceae family, Eucommiaceae family, Cannabaceae family and Urticaceae family can be mentioned other than Leguminosae family.

Hereinafter, the process for producing the PPAR ligand of the present invention from licorice is described as an example, but the starting material is not necessarily limited to licorice.

The usable licorice may be a plant of the genus *Glycyrrhiza* in the Leguminosae family, and examples thereof include *Glycyrrhiza uralensis* Fisch. et DC, *G. inflata* BAT., *G. glabra* L., *G. glabra* L. var *glandu rifera* Regel et Herder, *G. echinata* L., *G. pallidiflora* Maxim, and other plants of the same genus (Leguminosae). These plants are grown in, for example, Xin Jiang, Northeast China, Northwest China, Mongol, Russia, Afghanistan, Iran, Turkey, etc. Among them, those having a higher content of the PPAR ligand active ingredient, such as *G. uralensis* (growing areas: Northeast China, Northwest China, Mongol, Xin Jiang, etc.), *G. glabra* (growing areas: Russia, Afghanistan, Iran, Turkey, etc.) and *G. inflata* (growing areas: Xin Jiang, etc.) are preferable, and *G. uralensis* is particularly preferably used.

In the present invention, a root, a rhizome or a stolon of the licorice mentioned above is preferably used, and it is used in the form of a finely ground product, a ground product, a cut product or the periderm of the above-mentioned licorice. The finely ground product refers to a powdery or almost powdery product, and the ground product refers to a product in the form of filament, fiber or cotton (e.g. a product having a length of about 5 mm to about 10 cm). The cut product is one obtained by cutting a licorice root, a rhizome or a stolon (e.g. a thin round slice having a length of usually about 1 to 10 cm, preferably about 1 to 5 cm, more preferably about 2 to 4 cm, and a thickness of usually about 3 cm or less, preferably about 2 cm or less, more preferably about 1 cm or less) usually in a cylindrical form or a substantially cylindrical form. The finely ground product, ground product and cut product can be obtained by using a conventional apparatus. The finely ground product can be obtained as a powdery or almost powdery product by a Masscolloider type mill, grinding mortar, etc., and the ground product can be obtained by a grinding hammer mill or the like. The cut product can be obtained by cutting a root or the like of the licorice into pieces to have the above-mentioned length with a conventional cutting machine.

The composition and content of the active ingredient of the licorice vary to some degree depending on the species, growing area, harvest time, etc. thereof. Therefore, it is preferable to use one confirmed to contain a large amount of the active ingredient by a preliminary experiment.

The extraction methods include methods which comprise extracting the licorice with an organic solvent. But a water extraction residue obtained by extracting the licorice with water, or a dried product of the residue, may also be subjected to extraction with an organic solvent.

The organic solvent used herein is not particularly limited, but is preferably a safe one usable in producing and processing of pharmaceutical preparations, foods, food additives, etc. Examples thereof include acetone, a monohydric alcohol having 1 to 4 carbon atoms, glycerin, fatty acid esters, diethyl ether, cyclohexane, carbon dioxide, propylene glycol, etc., and two or more of these solvents may be used as a mixture. Solvents preferably used, among these, are fatty acid esters such as ethyl acetate, or water-soluble organic solvents such as a monohydric alcohol having 1 to 4 carbon atoms, acetone, propylene glycol, glycerin, etc., and particularly preferably the water-soluble organic solvents.

After extraction, it is preferable to increase the content of the active ingredient in the extract by purification such as adsorption treatment with an activated carbon, a resin or the like and/or fractionation. The material obtained by extraction may be subjected to column chromatography on a silica gel, ODS, an ion-exchange resin, etc., whereby the objective compound can be concentrated, fractionated or isolated.

As a matter of course, the objective compound can also be obtained by other chemical syntheses.

Hereinafter, a method of extracting licorice with a fatty acid ester or a water-soluble organic solvent is described in more detail as a preferable method of producing a licorice extract containing the PPAR ligand according to the present invention. The licorice extract extracted with a fatty acid ester or a water-soluble organic solvent tends to exhibit better PPAR ligand activity, and the water-soluble organic solvent is particularly preferably used because the PPAR ligand active substance can be efficiently obtained.

When the objective substance is extracted from the licorice with a fatty acid ester or a water-soluble organic solvent, a finely ground product, ground product, cut product or periderm of licorice may be extracted as it is, but as described above, a pre-extracted licorice residue obtained by preliminarily extracting from licorice with another solvent (e.g. water, an aqueous alkaline solution, etc.) may be extracted with a fatty acid ester or a water-soluble organic solvent to remove impurities, etc.

After pre-extraction from licorice with another solvent (water, an aqueous alkaline solution, etc.), the preliminary extract may be separated into an extract and an extracted licorice residue by a general separation procedure (e.g. filtration under pressure, vacuum filtration, filter press, centrifugation, sedimentation, etc.) to give a preliminarily extracted licorice residue. In this separation procedure, generally usable filter aids and/or adsorbents such as activated carbon and activated clay, etc. can be used if necessary.

The preliminarily extracted residue thus obtained is used in extraction with a fatty acid ester or a water-soluble organic solvent as such or after removal of a part or the whole of another solvent used (water, an aqueous alkaline solution, etc.) by a general drying procedure (e.g. drying in a stationary state, drying under stirring, mixing drying, drying in a fluidized state, flash drying, spray drying, freeze drying, freeze concentration, etc.).

The fatty acid ester or water-soluble organic solvent which can be preferably used in this extraction method includes, but is not limited to, acetates such as ethyl acetate, monohydric alcohols having 1 to 4 carbon atoms, acetone, propylene glycol, glycerin and mixtures thereof. Preferred among them are acetates such as ethyl acetate, monohydric alcohols having 1 to 4 carbon atoms, acetone or a mixture thereof, and more preferred are ethyl acetate, ethanol, acetone or mixtures thereof. In particular, ethanol is preferred in view of safety of the solvent to a human body. For reducing contamination with water-soluble impurities such as glycyrrhizin described later, a monohydric alcohol having 2 to 4 carbon atoms, fatty acid ester and acetone are preferred, fatty acid ester and acetone are particularly preferred, acetates and acetone are furthermore preferred, and ethyl acetate and acetone are still more preferred. Needless to say, other solvents may coexist in such a range as to be free of adverse effect.

In the present invention, it is important to increase the content of the active ingredient in a licorice extract, while reducing the content of water-soluble impurities such as glycyrrhizin.

Glycyrrhizin is also utilized as a pharmaceutical preparation, but has side effects such as increasing blood pressure, cardiovascular disorders and hydraemia (these three refer to Harders, H. & Rausch-Stroomann, J. G., Munch. Med. Wschr. 95, 580 (1953)), hypokalemia, a reduction in plasma renin activity, pseudo-aldosterone symptoms and extremities-relaxing paralysis (these four refer to Conn, J. W., Rovner, D. R. & Cohen, E. L., J. Am. Med. Assoc. 205, 492 (1968)), reduced secretion of aldosterone into urine, edema, headache and drowsiness (these four refer to Epstein, M. T., et al., Brit. Med. J., 1, 488 (1977)). And glycyrrhizin is 150 times as sweet as sucrose. Contamination with glycyrrhizin inhibits various effects of a licorice extract and causes side effects and strong sweetness, thus bringing about disadvantages in application to foods, etc.

For increasing the content of the active ingredient in the resulting licorice extract and reducing the content of water-soluble impurities such as glycyrrhizin at the same time, the content of water coexisting at the time of extraction with an organic solvent is preferably reduced. For reducing the content of water, it is important to use a licorice dried to the maximum degree, and also to use a water-free organic solvent.

However, needless to say, licorice is a plant, and conventional sun drying is not always enough to obtain sufficiently dried licorice, thus it becomes necessary to use a drying machine, etc. This is a serious weak point in production on a commercial scale.

Even if a water-free organic solvent is used, it is difficult to completely prevent the organic solvent from being contaminated with water from the licorice used and working atmosphere, and is thus recovered as an organic solvent increased in water content. Because the organic solvent is hardly recycled as it is, the solvent is discarded or special and expensive purification facilities for making it water-free are necessary, thus leading to an increase in production costs.

Accordingly, if a high-quality licorice extract with a higher content of the active ingredient and a lower content of water-soluble impurities can be produced quite easily and inexpensively, it is possible to expect significant advantages.

As a result of intensive study, the present inventors found that it is preferable to use licorice in such a form that the ratio of the skin area to the whole surface area thereof is high, usually 30% or more, preferably 50% or more, more preferably 70% or more, still more preferably 80% or more, further more preferably 90% or more (specifically, the cut product or the licorice periderm (including a product mainly comprising periderm)), in order to obtain a high-quality licorice extract. Furthermore, the inventors found that when the licorice in the above form is used, a high-quality licorice extract can be obtained even if a hydrated water-soluble organic solvent is used.

Between the cut product and the periderm (including a product mainly comprising periderm), the cut product is more preferably used since it can be processed more easily, and the ratio of the skin area to the whole surface area of the cut product is usually 50% or more, preferably 70% or more, more preferably 80% or more, and still more preferably 90% or more.

According to this method, the effect can be maximized when using particularly the above-mentioned water-soluble organic solvent, preferably a monohydric alcohol having 2 to 4 carbon atoms, more preferably ethanol.

The water content of the organic solvent used is usually about 30% by volume or less, preferably about 20% by volume or less, more preferably about 10% by volume or less, and still more preferably about 8% by volume or less. The lower limit is not particularly limited, but is usually about 3% by volume, preferably 4% by volume, from a practical point of view.

Thereby, a licorice extract having a higher content of the active ingredient and a lower content of water-soluble impurities can be preferably obtained. The content of glycyrrhizin in the resulting extract can be minimized preferably to 0.5% by weight or less. Even when an inexpensive hydrated water-soluble organic solvent is used as the extraction solvent, a high-quality extract can be preferably obtained (without specially drying the licorice).

Extraction with the fatty acid ester or the water-soluble organic solvent mentioned above can be carried out according to a general method, and is not particularly limited. The extraction temperature is not particularly limited, and extraction can be carried out preferably between the solidification temperature and the boiling point in the system, generally −20 to 100° C., usually 1 to 80° C., preferably 20 to 60° C.

The extraction procedure may be carried out, for example, for 0.1 hour or more, preferably 0.2 hour or more, more preferably 0.5 hour or more by using the fatty acid ester or the water-soluble organic solvent in, for example, 1- to 20-fold excess, preferably 2- to 10-fold excess, based on the volume of the licorice or the preliminarily extracted residue. Usually, the time for each extraction is preferably about 1 to 10 hours. The upper limit is not particularly limited and is about 1 day, but the extraction may be carried out for a longer time. Extraction may be carried out once or several times if necessary, and a suitably combined mixed solvent may be used. The pressure at the time of extraction is not particularly limited. Extraction is carried out at normal pressures or under pressure (one to several atmospheric pressure), but may be carried out under reduced pressure if desired. The extraction may be carried out under reflux or in a slightly pressurized state.

After the extraction, the preliminary extract can be separated into an extract and an extracted licorice residue by a general separation procedure (e.g. filtration under pressure, vacuum filtration, centrifugation, sedimentation, etc.) and if necessary washed with the solvent, to give a licorice extract. In the separation procedure, generally usable filter aids and/or adsorbents such as activated carbon, activated clay and resins can be used if necessary.

From the licorice extract thus obtained, the used solvent can be removed by a general procedure for solvent removal (e.g. concentration at normal pressure, vacuum concentration, spray drying, freeze drying, freeze concentration, etc.), whereby a solvent-free licorice extract can be obtained. After the extraction, the extract is more preferably purified by adsorption treatment with an activated carbon or a resin and/or fractionation thereby increasing the content of the active ingredient in the extract, as described above.

In the process of the present invention, a series of the above procedures, particularly extraction with a solvent, or extraction with a solvent and subsequent procedures (separation of an extract, removal of the solvent, adsorption treatment with an activated carbon, a resin or the like and/or fractionation, etc.), are preferably carried out under a deoxidized atmosphere such as an inert gas atmosphere using a nitrogen gas, etc. For the purpose of preventing oxidation, the process can be carried out in the concomitantly presence of antioxidants such as ascorbic acid, sodium ascorbate, ascorbyl palmitate, ascorbyl stearate, tocopherol, etc.

The licorice extract obtained after removal of a solvent is generally brown (e.g. yellowish brown to dark brown).

The weight ratio (dry weight basis) of the dry licorice extract obtained by the process to licorice as such is usually about 0.01 or more.

The content of glycyrrhizin in the extract of the present invention, on a dry weight basis, is as low as usually 0.5% by weight or less, preferably 0.3% by weight or less, more preferably 0.2% by weight or less, and still more preferably 0.1% by weight or less. When the content of glycyrrhizin in the extract of the present invention is 0.001 to 0.5% by weight on a dry weight basis, there is virtually not a problem in the side effects and disadvantages for use.

The content of glycyrrhizin in the extract can be determined by, for example, analysis with HPLC using commercial glycyrrhizin or glycyrrhizinate as a standard substance or the like analysis. The content of a PPAR ligand in the extract can be determined by, for example, analysis with HPLC using the PPAR ligand of the present invention as a standard substance or the like analysis. The PPAR ligand as a standard substance may be a compound isolated from a plant such as licorice or a chemically synthesized compound. The total amount of PPAR ligand components in the extract can be calculated as the total content of the quantified PPAR ligand components.

The total amount of the PPAR ligand components contained in the extract of the present invention, on a dry weight basis, is usually 0.5% by weight or more, preferably 1% by weight or more, and more preferably 2% by weight or more. In particular, when the PPAR ligand is extracted with a monohydric alcohol having 1 to 4 carbon atoms, its amount is usually 5% by weight or more, preferably 6% by weight or more, more preferably 7% by weight or more, thus indicating efficient recovery of the active ingredient. The total amount of the PPAR ligand components contained in the extract of the present invention, on a dry weight basis, is usually not higher than 50% by weight at the maximum, but the content can be further increased by adsorption treatment with an activated carbon, a resin or the like and/or fractionation.

For example, the extract of the present invention preferably comprises, for example, at least one species selected from the group consisting of glycycoumarin, glycyrin, dehydroglyasperin C, dehydroglyasperin D, glyasperin B and glyasperin D as a major component in an amount of usually 0.5% by weight or more, preferably 1% by weight or more, on a dry weight basis. More preferably, the extract comprises glycycoumarin, glycyrin, dehydroglyasperin C, dehydroglyasperin D, glyasperin B and glyasperin D respectively in an amount of usually 0.5% by weight or more, preferably 1% by weight or more, on a dry weight basis. These components are contained in a larger amount in an extract of licorice, particularly G. uralensis.

Additionally, the extract of the present invention preferably comprises, for example, at least one species selected from the group consisting of glycyrrhisoflavanone, glycyrrhisoflavone, glyurallin B, semilicoisoflavone B and isoliquiritigenin in an amount of usually 0.01% by weight or more, preferably 0.02% by weight or more, on a dry weight basis. More preferably, the extract comprises glycyrrhisoflavanone, glycyrrhisoflavone, glyurallin B, semilicoisoflavone B and isoliquiritigenin respectively in an amount of usually 0.01% by weight or more, preferably 0.02% by weight or more, on a dry weight basis.

Moreover, the extract of the present invention preferably comprises, for example, at least one species selected from the group consisting of glabrene, glabridin, glabrol, 3'-hydroxy-4'-O-methylglabridin, 4'-O-methylglabridin and hispaglabridin B in an amount of usually 0.5% by weight or more, preferably 1% by weight or more, on a dry weight basis. More preferably, the extract comprises glabrene, glabridin, glabrol, 3'-hydroxy-4'-O-methylglabridin, 4'-O-methylglabridin and hispaglabridin B respectively in an amount of usually 0.5% by weight or more, preferably 1% by weight or more, on a dry weight basis. These components are contained in a larger amount in an extract of licorice, particularly G. glabra.

Furthermore, the extract of the present invention preferably comprises, for example, at least one species selected from the group consisting of licochalcone A, licochalcone B, licochalcone C, glycyrdione A and glycyrdione C in an amount of usually 0.5% by weight or more, preferably 1% by weight or more, on a dry weight basis. More preferably, the extract more preferably comprises licochalcone A, licochalcone B, licochalcone C, glycyrdione A and glycyrdione C respectively in an amount of usually 0.5% by weight or more, preferably 1% by weight or more, on a dry weight basis. These components are contained in a larger amount in an extract of licorice, particularly *G. inflata*.

The composition for amelioration of insulin resistance or for prevention and/or amelioration of the insulin resistance syndrome of the present invention, and the composition for prevention and/or amelioration of inflammations or cancers of the present invention are compositions comprising the PPAR ligand of the present invention. That is, they are compositions which comprise at least one compound selected from the group consisting of a prenylflavonoid, a chalcone derivative exclusive of prenylflavonoids, a flavonol derivative exclusive of prenylflavonoids, and a salt, a glycoside and an esterified substance thereof acceptable as a pharmaceutical preparation or a food or a beverage.

As described above, the prenylflavonoid is not particularly limited, but is preferably at least one compound selected from the group consisting of a 3-arylcoumarin derivative, an isoflav-3-ene derivative, an isoflavan derivative, an isoflavanone derivative, an isoflavone derivative, a flavonol derivative, a flavanone derivative, a chalcone derivative and a dibenzoylmethane derivative.

The above compound may be a pure compound or a semi-purified or crude compound provided that it does not contain impurities unsuitable for pharmaceutical preparations and foods. In this case, the extract may be used as it is, or may be further purified. The compound is not limited in its form and can be used as, for example, foods or beverages such as health-promoting foods (specified healthful foods, nutrition functional foods), health foods and nutrition supplementary foods, pharmaceutical preparations, and quasi drugs.

The composition of the present invention can be administered to human, and also to domestic animals or pets such as dogs, cats, bovine species, equine species, swine species, chickens, sheep, goats, mice, and rats. For use as a food or a beverage, it can be directly ingested or may be formulated into easily ingestable products, such as capsules, tablets, granules, powders, etc., with the aid of a known carrier, an auxiliary agent or the like for ingestion. Furthermore, material for preparation other than the PPAR ligand of the present invention can be suitably added and mixed by a conventional method. Such material is not particularly restricted, and there may be mentioned, for example, excipients, disintegrators, lubricants, binders, antioxidants, coloring agents, aggregation inhibitors, absorption promoters, stabilizers, etc. The amount of the PPAR ligand of the present invention in such a formulated product may be 0.1 to 100% by weight preferably 10 to 90% by weight. Furthermore, it can be mixed into raw materials for all kinds of food or beverage products, for example, confections such as chewing gum, chocolate, candies, jellies, biscuits and crackers; frozen sweets such as ice cream and ice candies; beverages such as tea, nonalcoholic beverages, nutritional drinks, and drinks for beauty; noodles such as Japanese wheat noodles, Chinese noodles, spaghetti, and instant noodles; fish paste foods such as fish minced and steamed (kamaboko), fish sausage (chikuwa), and minced flesh (hannpen); seasonings such as dressings, mayonnaise and sauces; oleaginous products such as margarine, butter and salad oil; bakery products, hams, soups, retort foods, frozen foods, and so forth. In taking such a food or beverage composition, the recommended daily intake for an adult human is 0.1 to 3000 mg/kg, more preferably 1 to 300 mg/kg, as the PPAR ligand of the present invention. Such compositions can also be used as feeds for domestic animals and pets or as pet foods, and the recommended daily intake in these applications is preferably 0.1 to 3000 mg/kg as the PPAR ligand of the present invention.

For use as a pharmaceutical product, the dosage form is not particularly restricted but includes capsules, tablets, granules, powders, injections, suppositories, patches, etc. Such dosage forms can be prepared by suitably formulating pharmaceutically acceptable material for preparation such as excipients, disintegrators, lubricants, binders, antioxidants, coloring agents, aggregation inhibitors, absorption promoters, solubilizing agents and stabilizers. The daily dosage of such a preparation for adult human is 0.1 to 3000 mg/kg, preferably 1 to 300 mg/kg, as the PPAR ligand of the present invention, which dosage is to be administered once a day or in a few divided doses a day. The composition can also be used as a pharmaceutical product for domestic and pet animals and the daily dosage for this application is preferably 0.1 to 3000 mg/kg as the PPAR ligand of the present invention.

When the composition of the present invention is in the form of tablets, capsules or powders and when the above extract is contained as the PPAR ligand, the composition preferably comprises the extract in an amount of 0.1 to 1000 mg per tablet.

The PPAR ligand of the present invention is a plant-derived extract component or its related compound, and is considered to be low toxic. The extract obtained by the present invention can also be added to foods to which sweetness or the like is an obstacle. It is highly stable as compared with highly unsaturated fatty acids which are conventionally reported PPARγ ligands, and is superior in respect of a form suitable for foods and pharmaceutical compositions.

BEST MODE FOR CARRYING OUT THE INVENTION

Hereinafter, the present invention is described in more detail by reference to the Examples, but the scope of the present invention is not limited to these Examples.

EXAMPLE 1

Extraction and Isolation of a Compound from Licorice (1)

A finely ground product (1.2 kg) of licorice (*G. uralensis*) was immersed in 5.5 L of ethyl acetate and extracted for 7 days at room temperature with light-shielded. Then, the mixture was filtered to obtain an extract. The extract was concentrated under reduced pressure to remove the solvent, and 74.0 g of an extract was obtained. The extract obtained was subjected to silica gel column chromatography (1500 ml) to obtain a fraction eluted with chloroform:methanol=19:1 (v/v). The eluted fraction was concentrated under reduced pressure to remove the solvent, and 55.4 g of coarse fraction was obtained. This coarse fraction was purified by repeating silica gel column chromatography, ODS silica gel column chromatography, high performance liquid chromatography equipped with an ODS column, gel filtration column chromatography, and fractional thin layer chromatography. Thereby, Compound 1 (225 mg), Compound 2 (80.7 mg), Compound 3 (19.6 mg), Compound 4 (22.2 mg), Compound 5 (3.9 mg), Compound 6 (72.8 mg), Compound 7 (28.3 mg), Compound 8 (12.1 mg), Compound 9 (6.8 mg), Compound 10 (8.5 mg), Compound 11 (58.7 mg) and Compound 12 (10.2 mg) were obtained.

As the result of structural analysis, Compounds 1 to 3 and 5 to 12 are known compounds, and respectively identified as follows; Compound 1 was glycycoumarin, Compound 2 was glycyrin, Compound 3 was glyurallin B, Compound 5 was echinatin, Compound 6 was isolicoflavonol, Compound 7 was dehydroglyasperin C, Compound 8 was glyasperin B, Compound 9 was glycyrrhisoflavanone, Compound 10 was lupiwighteone, Compound 11 was glyasperin D, and Compound 12 was semilicoisoflavone B. Additionally, in the structural identification of these compounds, spectrum data described in S. Demizu, et al, Chemical and Pharmaceutical Bulletin, 36, 3474-3479 (1988) was referred to for Compound 1, T. Kinoshita, et al., Chemical and Pharmaceutical Bulletin, 26, 135-140 (1978) was referred to for Compound 2, M. Shibano, et al., Heterocycles, 45, 2053-2060 (1997) was referred to for Compounds 3 and 7, K. Kajiyama, et al., Phytochemistry, 31, 3229-3232 (1992) was referred to for Compound 5, T. Hatano, et al., Chemical and Pharmaceutical Bulletin, 36, 2090-2097 (1988) was referred to for Compounds 6 and 9, L. Zeng, et al., Heterocycles, 34, 575-587 (1992) was referred to for Compounds 8 and 11, Y. Hashidoko, et al., Agricultural and Biological Chemistry, 50, 1797-1807 (1986) was referred to for Compound 10, and F. Kiuchi, et al., Heterocycles, 31, 629-636 (1990) was referred to for Compound 12.

Compound 4 is a novel compound, and its structure was determined as 3-(2',4'-dihydroxyphenyl)-6-(3'',3''-dimethylallyl)-5,7-dimethoxy-2H-chromene by a spectrum analysis centered on dimensional NMR($^1$H-$^1$H COSY, HMQC, HMBC, PHNOESY), and named dehydroglyasperin D.

The characteristic and spectrum data of Compound 4 are as follows.

Dehydroglyasperin D, brown powder, $C_{22}H_{24}O_5$. EI-MS m/z: 368.1610[M]+(calculated value; $C_{22}H_{24}O_5$: 368.1624). Uvλmax (methanol) nm: 330 (logε=4.25), 243 sh (logε=4.21). IR(KBr tablet)cm$^1$: 3375, 2929, 1613, 1516, 1458, 1308, 1198, 1164, 1114, 1092, 1024, 978, 837. $^1$H-NMR(dimethyl disulfoxide) ppm: 7.06(1H, d, J=8.4 Hz, H-6'), 6.68(1H, s, H-4), 6.34(1H, d, J=2.3 Hz, H-3'), 6.33(1H, s, H-8), 6.26(1H, dd, J=8.4, 2.3 Hz, H-5'), 5.09(1H, br t, J=6.9 Hz, H-10), 4.90(2H, s, H-2), 3.75(3H, s, C-7-OMe), 3.67(3H, s, C-5-OMe), 3.18(2H, br d, J=6.7 Hz, H-9), 1.71(3H, s, Me-13), 1.63(3H, s, Me-12). $^{13}$C-NMR(dimethyl disulfoxide) ppm: 67.9(C-2), 128.8(C-3), 114.7(C-4), 110.4(C-4a), 154.9(C-5), 115.6(C-6), 158.0(C-7), 95.8(C-8), 153.2(C-8a), 22.6(C-9), 124.1(C-10), 130.4(C-11), 26.0(C-12), 18.1(C-13), 116.8(C-1'), 156.7(C-2'), 103.3(C-3'), 158.7(C-4'), 107.4 (C-5'), 129.2(C-6'), 62.3(C-5-OMe), 56.3(C-7-OMe).

EXAMPLE 2

Extraction and Isolation of a Compound from Licorice (2)

In the same procedure as in Example 1, Compounds 13 to 17 were obtained by extracting a finely ground product of licorice (*G. uralensis*) with ethanol to carry out various chromatography. As a result of structural analysis, the Compounds were identified as follows; Compound 13 was isoliquiritigenin, Compound 14 was kaempferol 3-O-methyl ester, Compound 15 was licoflavonol, Compound 16 was topazolin, and Compound 17 was glycyrrisoflavone.

EXAMPLE 3

Extraction and Isolation of a Compound from Licorice (3)

In the same procedure as in Example 1 or 2, Compounds 18 to 23 and Compounds 24 to 28 were obtained by extracting a finely ground product of licorice (*G. glabra*) and a finely ground product of licorice (*G. inflata*) with ethanol, respectively. As a result of structural analysis, the Compounds were identified as follows; Compound 18 was glabridin, Compound 19 was glabrene, Compound 20 was hispaglabridin B, Compound 21 was 4'-O-methylglabridin, Compound 22 was 3'-hydroxy-4'-O-methylglabridin, Compound 23 was glabrol, Compound 24 was licochalcone A, Compound 25 was licochalcone B, Compound 26 was licochalcone C, Compound 27 was glycyrdione A, and Compound 28 was glycyrdione C.

Tables 10 to 13 show the structural formulae of Compounds 1 to 28.

TABLE 10

| Compound number | Compound name | Structural formula |
|---|---|---|
| Compound 1 | Glycycoumarin | |
| Compound 2 | Glycyrin | |

TABLE 10-continued

| Compound number | Compound name | Structural formula |
| --- | --- | --- |
| Compound 3 | Glyurallin B | |
| Compound 4 | Dehydroglyasperin D | |
| Compound 5 | Echinatin | |
| Compound 6 | Isolicoflavonol | |
| Compound 7 | Dehydroglyasperin C | |
| Compound 8 | Glyasperin B | |

TABLE 11
| Compound number | Compound name | Structural formula |
| --- | --- | --- |
| Compound 9 | Glycyrrhisoflavanone | 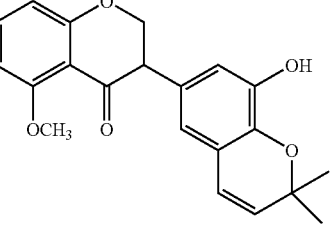 |
| Compound 10 | Lupiwighteone | 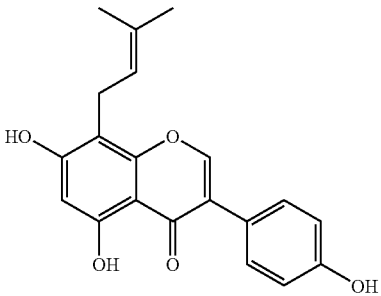 |
| Compound 11 | Glyasperin D | 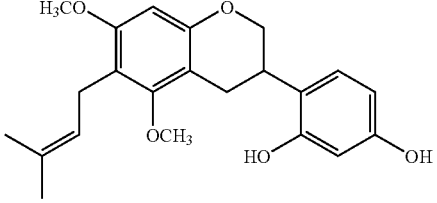 |
| Compound 12 | Semilicoisoflavone B | 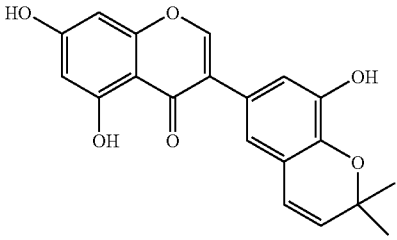 |
| Compound 13 | Isoliquiritigenin | 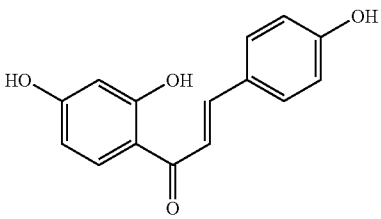 |
| Compound 14 | Kaempferol 3-O-methylester | 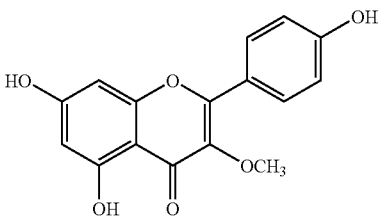 |

TABLE 11-continued
| Compound number | Compound name | Structural formula |
| --- | --- | --- |
| Compound 15 | Licoflavonol | 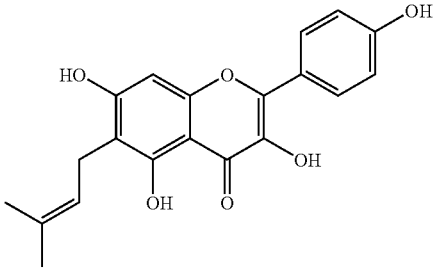 |
TABLE 12
| Compound number | Compound name | Structural formula |
| --- | --- | --- |
| Compound 16 | Topazolin | 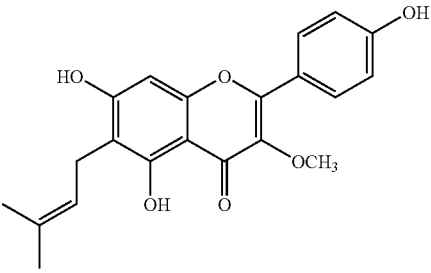 |
| Compound 17 | Glycyrrhisoflavone | 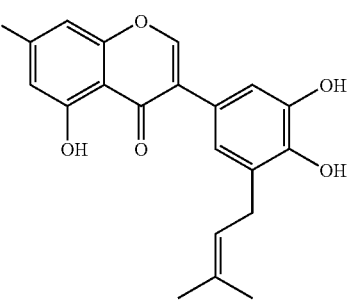 |
| Compound 18 | Glabridin | 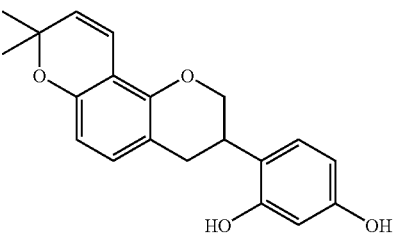 |
| Compound 19 | Glabrene | 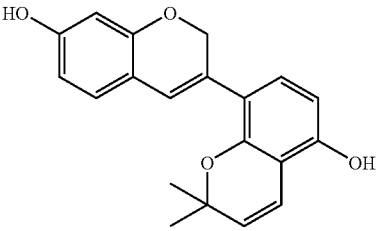 |

TABLE 12-continued

| Compound number | Compound name | Structural formula |
| --- | --- | --- |
| Compound 20 | Hispaglabridin B | |
| Compound 21 | 4'-O-Methylglabridin | |
| Compound 22 | 3'-Hydroxyl-4'-O-methylglabridin | |

TABLE 13

| Compound number | Compound name | Structural formula |
| --- | --- | --- |
| Compound 23 | Glabrol | |

TABLE 13-continued

| Compound number | Compound name | Structural formula |
|---|---|---|
| Compound 24 | Licochalcone A | |
| Compound 25 | Licochalcone B | |
| Compound 26 | Licochalcone C | |
| Compound 27 | Glycyrdione A | |
| Compound 28 | Glycyrdione C | |

EXAMPLE 4

Measurement of PPARγ Ligand Activity

CV-1 cells (cultured cells derived from the kidney of a male African green monkey) were inoculated on a 96-well culture plate in a concentration of $6 \times 10^3$ cells/well and incubated at 37° C. in 5% $CO_2$ for 24 hours. The medium used was DMEM (Dulbecco's Modified Eagle Medium: GIBCO) containing 10% FBS (fetal bovine serum), 10 ml/L penicillin and streptomycin solution (containing 5000 IU/ml and 5,000 μg/ml, respectively: GIBCO) and 37 mg/L ascorbic acid (Wako Pure Chemical Industries, Ltd.). The cells were washed with OPTI-MEM (GIBCO) and then transfected with pM-mPPARγ and 4xxUASg-luc by means of Lipofect Amine Plus (GIBCO). pM-mPPARγ is a plasmid for chimera protein expression comprising yeast-derived transcription factor GAL4 gene (amino acid sequence at 1 to 147) and a mouse PPARγ ligand-binding site gene (amino acid sequence at 174 to 475) bound thereto. 4xUASg-luc is a reporter plasmid comprising four GAL4 response sequences (UASg) integrated into a region upstream of a luciferase gene. At about 24 hours after transfection, the medium was exchanged with a sample-containing medium, and the cells were cultured for 24 hours (n=4). The sample-containing medium was prepared by dissolving a sample in dimethyl sulfoxide (DMSO) in an amount of 1/1000 based on the medium, while for the untreated control, DMSO in an amount of 1/1000 based on the medium was used in place of the sample. After the cells were washed with a Ca- and Mg-containing phosphate buffered physiological saline (PBS+), LucLite (Packard) was added thereto, and the intensity of luciferase luminescence was measured with a TopCount microplate scintillation/luminescence counter (Packard).

As the control group, pM (plasmid from which the PPARγ ligand-binding site gene was removed) was measured in place of pM-mPPARγ in the same manner as for the measurement group. For each sample, the ratio (measurement group/control group) of the average luminescence intensity of the measurement group (n=4) to that of the control group was calculated, and the specific activity relative to the activity of the untreated control was regarded as the PPARγ ligand activity of the sample.

Tables 14 to 17 show the measurement results of the PPARγ ligand activities of Compounds 1 to 28 obtained in Examples 1 to 3. As comparative compounds, glycyrrhizin (glycyrrhizic acid, Wako Pure Chemical Industries, Ltd.), glycyrrhetinic acid (Wako Pure Chemical Industries, Ltd.) and quercetin (Sigma) were measured for their PPARγ ligand activity.

TABLE 14

| | Added concentration | PPARγ ligand activity |
|---|---|---|
| Untreated control (DMSO) | 0.1% | 1.00 |
| Troglitazone | 0.5 μM | 2.17 ± 0.08 |
| | 1 μM | 3.36 ± 0.24 |
| | 2 μM | 4.60 ± 0.27 |
| Compound 1 (Glycycoumarin) | 2 μg/ml (5.4 μM) | 2.03 |
| | 5 μg/ml (13.6 μM) | 2.79 |
| | 10 μg/ml (27.2 μM) | 3.82 |
| Compound 2 (Glycyrin) | 2 μg/ml (5.2 μM) | 2.81 |
| | 5 μg/ml (13.1 μM) | 3.34 |
| | 10 μg/ml (26.2 μM) | 3.67 |
| Compound 3 (Glyurallin B) | 2 μg/ml (4.7 μM) | 1.28 |
| | 5 μg/ml (11.8 μM) | 1.96 |
| | 10 μg/ml (23.7 μM) | 2.73 |
| Compound 4 (Dehydroglyasperin D) | 2 μg/ml (5.4 μM) | 2.95 |
| | 5 μg/ml (13.6 μM) | 3.72 |
| | 10 μg/ml (27.2 μM) | 4.00 |
| Compound 5 (Echinatin) | 2 μg/ml (7.4 μM) | 1.45 |
| | 5 μg/ml (18.5 μM) | 2.35 |
| | 10 μg/ml (37.0 μM) | 2.49 |

TABLE 15

| | Added concentration | PPARγ ligand activity |
|---|---|---|
| Untreated control (DMSO) | 0.1% | 1.00 |
| Troglitazone | 0.5 μM | 2.44 ± 0.10 |
| | 1 μM | 3.99 ± 0.24 |
| | 2 μM | 5.74 ± 0.31 |
| Compound 6 (Isocoflavonol) | 2 μg/ml (5.6 μM) | 1.73 |
| | 5 μg/ml (14.1 μM) | 2.50 |
| | 10 μg/ml (28.2 μM) | 3.82 |

TABLE 15-continued

| | Added concentration | PPARγ ligand activity |
|---|---|---|
| Compound 7 (Dehydroglyasperin C) | 2 μg/ml (5.6 μM) | 2.90 |
| | 5 μg/ml (14.1 μM) | 3.73 |
| | 10 μg/ml (28.2 μM) | 4.41 |
| Compound 8 (Glyasperin B) | 2 μg/ml (5.4 μM) | 2.60 |
| | 5 μg/ml (13.5 μM) | 3.53 |
| | 10 μg/ml (27.0 μM) | 3.02 |
| Compound 9 (Glycyrrhisoflavanone) | 2 μg/ml (5.4 μM) | 2.01 |
| | 5 μg/ml (13.6 μM) | 3.45 |
| | 10 μg/ml (27.2 μM) | 4.68 |
| Compound 10 (Lupiwighteone) | 2 μg/ml (5.9 μM) | 1.67 |
| | 5 μg/ml (14.8 μM) | 2.53 |
| | 10 μg/ml (29.6 μM) | 3.75 |
| Compound 11 (Glyasperin D) | 2 μg/ml (5.4 μM) | 3.22 |
| | 5 μg/ml (13.5 μM) | 3.28 |
| | 10 μg/ml (27.0 μM) | 4.06 |
| Compound 12 (Semilicoisoflavone B) | 2 μg/ml (5.7 μM) | 1.86 |
| | 5 μg/ml (14.2 μM) | 2.66 |
| | 10 μg/ml (28.4 μM) | 3.15 |
| Glycyrrhizin | 2 μg/ml (2.4 μM) | 1.21 |
| | 5 μg/ml (6.1 μM) | 1.10 |
| | 10 μg/ml (12.2 μM) | 0.75 |
| Glycyrrhetinic acid | 2 μg/ml (4.2 μM) | 0.97 |
| | 5 μg/ml (10.6 μM) | 0.95 |
| | 10 μg/ml (21.2 μM) | 0.97 |
| Quercetin | 2 μg/ml (5.9 μM) | 1.15 |
| | 5 μg/ml (14.8 μM) | 1.72 |
| | 10 μg/ml (29.6 μM) | 1.70 |

TABLE 16

| | Added concentration | PPARγ ligand activity |
|---|---|---|
| Untreated control (DMSO) | 0.1% | 1.00 |
| Troglitazone | 0.5 μM | 2.24 ± 0.56 |
| | 1 μM | 3.29 ± 0.60 |
| | 2 μM | 4.80 ± 1.30 |
| Compound 13 (Isoliquiritigenin) | 2 μg/ml (7.8 μM) | 1.47 |
| | 5 μg/ml (19.5 μM) | 2.71 |
| | 10 μg/ml (39.0 μM) | 3.39 |
| Compound 14 (Kaempferol 3-O-methylester) | 2 μg/ml (6.7 μM) | 1.86 |
| | 5 μg/ml (16.7 μM) | 2.37 |
| | 10 μg/ml (33.3 μM) | 3.47 |
| Compound 15 (Licoflavonol) | 2 μg/ml (5.6 μM) | 1.44 |
| | 5 μg/ml (14.1 μM) | 2.27 |
| | 10 μg/ml (28.2 μM) | 4.07 |
| Compound 16 (Topazolin) | 2 μg/ml (5.4 μM) | 2.56 |
| | 5 μg/ml (13.6 μM) | 3.64 |
| | 10 μg/ml (27.1 μM) | 5.84 |
| Compound 17 (Glycyrrhisoflavone) | 2 μg/ml (5.6 μM) | 1.78 |
| | 5 μg/ml (14.1 μM) | 3.05 |
| | 10 μg/ml (28.2 μM) | 3.20 |

TABLE 17

| | Added concentration | PPARγ ligand activity |
|---|---|---|
| Untreated control (DMSO) | 0.1% | 1.00 |
| Troglitazone | 0.5 μM | 2.05 ± 0.35 |
| | 1 μM | 3.30 ± 0.43 |
| | 2 μM | 5.66 ± 1.06 |
| Compound 18 (Glabridin) | 2 μg/ml (6.2 μM) | 1.64 |
| | 5 μg/ml (15.4 μM) | 2.15 |
| | 10 μg/ml (30.8 μM) | 1.98 |
| Compound 19 (Glabrene) | 2 μg/ml (6.2 μM) | 1.78 |
| | 5 μg/ml (15.5 μM) | 3.44 |
| | 10 μg/ml (31.0 μM) | 2.89 |
| Compound 20 (Hispaglabridin B) | 2 μg/ml (5.1 μM) | 1.04 |
| | 5 μg/ml (12.8 μM) | 1.45 |
| | 10 μg/ml (25.6 μM) | 1.94 |

TABLE 17-continued

| | Added concentration | PPARγ ligand activity |
|---|---|---|
| Compound 21 (4'-O-Methylglabridin) | 2 μg/ml (5.9 μM) | 1.25 |
| | 5 μg/ml (14.8 μM) | 1.55 |
| | 10 μg/ml (29.6 μM) | 2.13 |
| Compound 22 (3'-Hydroxyl-4'-O-methylglabridin) | 2 μg/ml (5.6 μM) | 1.61 |
| | 5 μg/ml (14.1 μM) | 2.46 |
| | 10 μg/ml (28.2 μM) | 1.69 |
| Compound 23 (Glabrol) | 2 μg/ml (5.1 μM) | 1.85 |
| | 5 μg/ml (12.7 μM) | 3.48 |
| | 10 μg/ml (25.5 μM) | 3.74 |
| Compound 24 (Licochalcone A) | 2 μg/ml (5.9 μM) | 4.02 |
| | 5 μg/ml (14.8 μM) | 4.14 |
| | 10 μg/ml (29.6 μM) | 4.16 |
| Compound 25 (Licochalcone B) | 2 μg/ml (7.0 μM) | 1.27 |
| | 5 μg/ml (17.5 μM) | 1.93 |
| | 10 μg/ml (34.9 μM) | 1.61 |
| Compound 26 (Licochalcone C) | 2 μg/ml (5.9 μM) | 1.84 |
| | 5 μg/ml (14.8 μM) | 2.20 |
| | 10 μg/ml (29.6 μM) | 3.71 |
| Compound 27 (Glycyrdione A) | 2 μg/ml (4.9 μM) | 1.44 |
| | 5 μg/ml (12.2 μM) | 2.49 |
| | 10 μg/ml (24.5 μM) | 3.05 |
| Compound 28 (Glycyrdione C) | 2 μg/ml (4.9 μM) | 0.96 |
| | 5 μg/ml (12.3 μM) | 1.48 |
| | 10 μg/ml (24.6 μM) | 2.04 |

The above PPARγ ligand activity of each compound was compared with that of a positive control, troglitazone (Sankyo Co., Ltd.). As a result, Compounds 1 to 19, 21 to 24, 26 and 27 were recognized to have higher PPARγ ligand activity than that of a positive control containing 0.5 μM troglitazone. Compounds 20, 25 and 28 were also recognized to have PPARγ ligand activity, although it was slightly weaker than that of a positive control containing 0.5 μM troglitazone. However, glycyrrhizin that is a hydrophilic component and a major component of licorice, glycyrrhetinic acid (derivative of glycyrrhizin whose sugar residue was hydrolyzed), and quercetin (flavonol derivative of Compound 6 in which OH group substitutes prenyl group), were not recognized to have a PPARγ ligand activity. The fact that quercetin does not have a PPARγ ligand activity accords with information in a literature (Liang, Y. C., et al., FEBS Letters, 496, 12-18, 2001).

EXAMPLE 5

Effect on Type 2 Diabetes Mellitus Model Mouse

Using a KK-Ay mouse which is genetically obese and type 2 diabetic animal, the effect of Compound 2 on diabetes mellitus was evaluated. For a positive control, pioglitazone, i.e. an agent for ameliorating insulin resistance/agent for treating type 2 diabetes mellitus was used.

KK-Ay mice (female, 15-week-old) were divided into 3 groups each consisting of 5 mice, and freely given a feed comprising only a basal diet, i.e. powdered CE-2 (CLEA Japan, Inc.), to a non-additive group (control group), a feed comprising a basal diet and pioglitazone to a pioglitazone-given group, and a feed comprising a basal diet and Compound 2 to a Compound 2-given group. As for pioglitazone, ACTOS Tablet 30 (containing 30 mg pioglitazone per tablet, Takeda Chemical Industries, Ltd.) was milled with an agate mortar and added to the basal diet such that the content of pioglitazone in a final feed was 0.02%. Compound 2 was prepared in the same procedure as in Example 1 and added to the basal diet such that the content of Compound 2 in a final feed was 0.1%. On the day before administration and 4 days after administration, a small amount of blood was collected from a mouse tail vein, and measured for its blood glucose level by a simple blood glucose measuring instrument Glutest Ace (Sanwa Kagaku Kenkyusho Co., Ltd.). Table 18 shows the results.

After the mixed feed was given for 1 week, the mice were fasted overnight and then subjected to a glucose tolerance test. That is, 20 mg/kg of pioglitazone, or 100 mg/kg of Compound 2, suspended in 0.5% carboxymethyl cellulose-sodium (CMC-Na) solution, was forcibly orally administered into the fasted mice. To the non-additive group (control group), 0.5% CMC-Na solution was administered in an amount of 5 ml/kg. At a time of 30 minutes after administration, the mice were loaded with 2 g/kg of 40% sucrose solution. Before the sugar loading and at a time of 30 minutes, 1 hour and 2 hours after the sugar loading, a small amount of blood was collected from a mouse tail vein, and measured for its blood glucose level by a simple blood glucose measuring instrument Glutest Ace (Sanwa Kagaku Kenkyusho Co., Ltd.). Table 19 shows the results.

TABLE 18

| Blood glucose level (mg/dl) | Non-additive group (control group) | Pioglitazone-given group | Compound 2 (Glycyrin)-given group |
|---|---|---|---|
| Before administration | 476 ± 22 | 486 ± 26 | 474 ± 27 |
| 4 days after administration | 420 ± 14 | 191 ± 6 ** | 278 ± 14 ** |

** ($p < 0.01$)

TABLE 19

| Blood glucose level (mg/dl) | Non-additive group (control group) | Pioglitazone-given group | Compound 2 (Glycyrin)-given group |
|---|---|---|---|
| Before sugar loading | 80 ± 2 | 89 ± 3 | 78 ± 4 |
| 30 minutes after sugar loading | 355 ± 18 | 158 ± 11 ** | 225 ± 27 ** |
| 1 hour after sugar loading | 199 ± 11 | 136 ± 5 * | 129 ± 8 * |
| 2 hour after sugar loading | 100 ± 4 | 106 ± 4 | 100 ± 3 |

* ($p < 0.05$),
** ($p < 0.01$)

As is evident from Table 18, the blood glucose levels (means±SE, n=5) of the mice of Compound 2-given group were statistically significantly reduced in a similar manner as in that of the mice of pioglitazone-given group, on the fourth day after the administration. As is evident from Table 19, Compound 2, like pioglitazone, has statistically significantly inhibited a rapid increase in blood glucose levels after the sugar loading. From these results, it was confirmed that Compound 2 has a lowering action and an increase-inhibition action of blood glucose level, thus was suggested that the compound has an insulin resistance-ameliorating action, like pioglitazone.

EXAMPLE 6

A finely ground product (500 g) of licorice (*G. uralensis*) (Kaneka Sun Spice Co., Ltd) was added with 5 kg of ethanol (99.5% by volume). The mixture was extracted at 25° C. for 5 hours, and the residue was filtered off to obtain an extract. The solvent was removed from this extract under reduced pressure, and 45 g of a licorice extract having a color of yellow brown to dark brown was obtained. This licorice extract exhibited good PPARγ ligand activity. Table 20 shows contents of PPARγ ligand active ingredients and glycyrrhizin contained in this licorice extract.

Additionally, the contents of these active ingredients and glycyrrhizin were obtained by the HPLC analysis under the following conditions.

(Glycyrrhizin Analysis Conditions)

Column; J'sphere ODS-H80 (YMC Co., Ltd.) 4.6 mm (inner diameter)×250 mm (length): column temperature; 40° C.: mobile phase; acetonitrile/10 mM phosphoric acid solution=33/67 (v/v): flow rate; 1 ml/min: detection wavelength; 254 nm: retention time of glycyrrhizin; 27.1 min.

(Active Ingredient Analysis Conditions)

Column; J'sphere ODS-H80 (YMC Co., Ltd.) 4.6 mm (inner diameter)×250 mm (length): column temperature; 40° C. Mobile phase; A gradient in which the ratio of acetonitrile relative to a 10 mM phosphoric acid solution is kept to be 35% untill 15 min after the start of analysis, then increased to 70% at a constant rate in a period from 15 min until 65 min, and then kept to be 70% in a period from 65 min until 70 min. Flow rate; 1 ml/min, detection wavelength; 254 nm. Retention time for each component is as follows; 5.2 min for licochalcone B, 13.3 min for glycyrrhisoflavanone, 14.7 min for isoliquiritigenin, 32.7 min for glycycoumarin, 34.2 min for semilicoisoflavone B, 35.9 min for glabrene, 36.3 min for glycyrrhisoflavone, 37.2 min for dehydroglyasperin C, 39.1 min for licochalcone C, 40.2 min for licochalcone A, 44.7 min for glabridin, 48.1 min for glycyrin, 51.1 min for glyasperin B, 51.8 min for glabrol, 52.7 min for glyasperin D, 53.4 min for glycyrdione A, 53.5 min for 3'-hydroxyl-4'-O-methylglabridin, 55.2 min for dehydroglyasperin D, 58.7 min for glyurallin B, 59.8 min for 4'-O-methylglabridin, 63.0 min for glycyrdione C, and 74.1 min for hispaglabridin B.

TABLE 20

| Compound name | Content (wt %) |
| --- | --- |
| Glycyrrhizin | 0.28 |
| Glycyrrhisoflavanone | 0.15 |
| Isoliquiritigenin | 0.19 |
| Glycycoumarin | 2.55 |
| Semilicoisoflavone B | 0.45 |
| Glycyrrhisoflavone | 0.50 |
| Dehydroglyasperin C | 2.82 |
| Glycyrin | 1.46 |
| Glyasperin B | 1.12 |
| Glyasperin D | 2.44 |
| Dehydroglyasperin D | 1.39 |
| Glyurallin B | 0.03 |
| Active component: total | 13.10% |

EXAMPLE 7

A licorice extract (18 g) was obtained by the same procedure as in Example 6 except that extraction was carried out by acetone instead of ethanol. The obtained licorice extract exhibited good PPARγ ligand activity. Contents of active ingredients and glycyrrhizin contained in this licorice extract were examined in the same manner as in Example 6, and Table 21 shows the results.

TABLE 21

| Compound name | Content (wt %) |
| --- | --- |
| Glycyrrhizin | 0.06 |
| Glycyrrhisoflavanone | 0.19 |
| Isoliquiritigenin | 0.16 |
| Glycycoumarin | 3.50 |
| Semilicoisoflavone B | 0.01 |
| Glycyrrhisoflavone | 0.69 |
| Dehydroglyasperin C | 4.09 |
| Glycyrin | 1.91 |
| Glyasperin B | 1.40 |
| Glyasperin D | 3.38 |
| Dehydroglyasperin D | 1.82 |
| Glyurallin B | 0.03 |
| Active component: total | 17.18% |

EXAMPLE 8

A licorice extract (18 g) was obtained by the same procedure as in Example 6 except that extraction was carried out by ethyl acetate instead of ethanol. The obtained licorice extract exhibited good PPARγ ligand activity. Contents of active ingredients and glycyrrhizin contained in this licorice extract were examined in the same manner as in Example 6, and Table 22 shows the results.

TABLE 22

| Compound name | Content (wt %) |
| --- | --- |
| Glycyrrhizin | 0.05 |
| Glycyrrhisoflavanone | 0.18 |
| Isoliquiritigenin | 0.09 |
| Glycycoumarin | 3.44 |
| Semilicoisoflavone B | 0.62 |
| Glycyrrhisoflavone | 0.70 |
| Dehydroglyasperin C | 4.09 |
| Glycyrin | 1.96 |
| Glyasperin B | 1.52 |
| Glyasperin D | 3.41 |
| Dehydroglyasperin D | 1.93 |
| Glyurallin B | 0.03 |
| Active component: total | 17.97% |

COMPARATIVE EXAMPLE 1

A licorice extract was obtained by the same procedure as in Example 6 except that extraction was carried out by water instead of ethanol. This licorice extract exhibited no PPARγ ligand activity.

EXAMPLE 9

A finely ground product (500 g) of licorice (G. uralensis) (Kaneka Sun Spice Co., Ltd) was added with 5 kg of water, and the mixture was extracted at 60° C. for 1 day. Then, the residue was filtered off and dried under reduced pressure. The obtained pre-extracted residue was added with 2.5 kg of ethanol (99.5% by volume) and then extracted at 25° C. for 5 hours, and the residue was filtered off to obtain an extract. The solvent was removed from this extract under reduced pressure, and 47 g of a licorice extract having a color of yellow brown to dark brown was obtained. This licorice extract exhibited good PPARγ ligand activity. Table 23 shows contents of PPARγ ligand active ingredients and glycyrrhizin contained in this licorice extract.

TABLE 23

| Compound name | Content (wt %) |
|---|---|
| Glycyrrhizin | 0.50 |
| Glycyrrhisoflavanone | 0.18 |
| Isoliquiritigenin | 1.93 |
| Glycycoumarin | 2.10 |
| Semilicoisoflavone B | 0.40 |
| Glycyrrhisoflavone | 0.44 |
| Dehydroglyasperin C | 1.19 |
| Glycyrin | 1.44 |
| Glyasperin B | 1.19 |
| Glyasperin D | 1.59 |
| Dehydroglyasperin D | 1.03 |
| Glyurallin B | 0.03 |
| Active component: total | 11.52% |

EXAMPLE 10

Licorice extracts (25.8 g and 29.5 g) were obtained by extracting cut products (the ratio of the total surface area of skin is about 80% of the total surface area of licorice) of licorice (*G. uralensis*) with 99.5% by volume and 95.0% by volume of ethanol (water contents were 0.5 and 5.0% by volume, respectively), respectively, in the same procedure as in Example 6. These licorice extracts exhibited good PPARγ ligand activity. Table 24 shows contents of PPARγ ligand active ingredients and glycyrrhizin contained in these licorice extracts.

TABLE 24

| Water content ratio of ethanol at the time of extraction<br>Compound name | 0.5 vol %<br>Content (wt %) | 5.0 vol %<br>Content (wt %) |
|---|---|---|
| Glycyrrhizin | 0.02 | 0.26 |
| Glycyrrhisoflavanone | 0.14 | 0.03 |
| Isoliquiritigenin | 0.03 | 0.05 |
| Glycycoumarin | 3.12 | 2.85 |
| Semilicoisoflavone B | 0.42 | 0.41 |
| Glycyrrhisoflavone | 0.65 | 0.54 |
| Dehydroglyasperin C | 7.53 | 4.50 |
| Glycyrin | 1.95 | 1.92 |
| Glyasperin B | 3.92 | 3.62 |
| Glyasperin D | 6.48 | 4.23 |
| Dehydroglyasperin D | 4.43 | 3.63 |
| Glyurallin B | 0.12 | 0.11 |
| Active component: total | 28.79% | 21.89% |

EXAMPLE 11

A licorice extract was obtained from a finely ground product of licorice (*G. glabra*) in the same procedure as in Example 6. Contents of active ingredients and glycyrrhizin contained in this licorice extract were examined in the same manner as in Example 6, and Table 25 shows the results.

TABLE 25

| Compound name | Content (wt %) |
|---|---|
| Glycyrrhizin | 0.27 |
| Glycyrrhisoflavanone | 0.09 |
| Isoliquiritigenin | 0.12 |
| Glabrene | 3.14 |
| Glabridin | 22.08 |
| Glabrol | 4.33 |
| 3'-Hydroxyl-4'-O-methylglabridin | 2.19 |
| 4'-O-Methylglabridin | 3.03 |
| Hispaglabridin B | 1.14 |
| Active component: total | 36.12% |

EXAMPLE 12

A licorice extract was obtained from a finely ground product of licorice (*G. inflata*) in the same procedure as in Example 0.6. The obtained licorice extract exhibited good PPARγ ligand activity. Contents of active ingredients and glycyrrhizin contained in this licorice extract were examined in the same manner as in Example 6, and Table 26 shows the results.

TABLE 26

| Compound name | Content (wt %) |
|---|---|
| Glycyrrhizin | 0.17 |
| Isoliquiritigenin | 0.19 |
| Licochalcone B | 2.57 |
| Licochalcone C | 3.61 |
| Licochalcone A | 20.34 |
| Glycyrdione A | 1.91 |
| Glycyrdione C | 0.94 |
| Active component: total | 29.56% |

EXAMPLE 13

Corn starch, lactose, carboxylmethyl cellulose, and magnesium stearate were mixed with the licorice extract obtained in Example 6. Furthermore, an aqueous solution of polyvinyl pyrrolidone was added thereto as a binder, and the mixture was granulated by a conventional method. The resultant was added with talc and mixed, and was pressed into tablets having the following compositions.

| | |
|---|---|
| Licorice extract | 10 parts by weight |
| Corn starch | 25 parts by weight |
| Lactose | 15 parts by weight |
| Carboxylmethyl cellulose | 10 parts by weight |
| Magnesium stearate | 3 parts by weight |
| Polyvinyl pyrrolidone | 5 parts by weight |
| Talc | 10 parts by weight |

INDUSTRIAL APPLICABILITY

According to the present invention, a peroxisome proliferator-activated receptor (PPAR) ligand, and a composition containing thereof can be provided easily and efficiently. The composition of the present invention is useful for amelioration of insulin resistance or as an agent for prevention and/or amelioration of the insulin resistance syndrome.

The invention claimed is:

1. A compound represented by the formula:

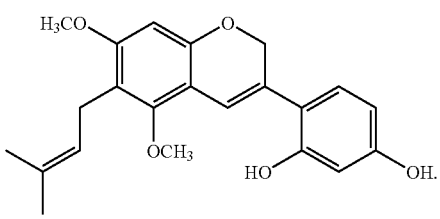

* * * * *